US007745645B2

(12) United States Patent
Frank et al.

(10) Patent No.: US 7,745,645 B2
(45) Date of Patent: Jun. 29, 2010

(54) SULFONAMIDE DERIVATIVES OF XANTHENE COMPOUNDS

(75) Inventors: Wilhelm G. Frank, Jena (DE);
Matthias S. Wenzel, Jena (DE); Peter T. Czerney, Weimar (DE); Surbhi Desai, Rockford, IL (US); Greg Hermanson, Loves Park, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 813 days.

(21) Appl. No.: 11/625,379

(22) Filed: Jan. 22, 2007

(65) Prior Publication Data
US 2008/0177086 A1    Jul. 24, 2008

(51) Int. Cl.
C07D 311/90 (2006.01)
C07D 405/10 (2006.01)
C12Q 1/68 (2006.01)
(52) U.S. Cl. .................. 549/227; 549/394; 548/525; 435/6; 435/7.1; 436/172; 436/546; 436/800; 530/404; 536/25; 536/32
(58) Field of Classification Search ........... 549/227; 548/525; 435/6, 7.1; 436/546, 172, 800; 530/404; 536/25.32
See application file for complete search history.

(56) References Cited
U.S. PATENT DOCUMENTS

| 5,268,486 | A | 12/1993 | Waggoner et al. |
| 5,486,616 | A | 1/1996 | Waggoner et al. |
| 5,569,587 | A | 10/1996 | Waggoner |
| 5,569,766 | A | 10/1996 | Waggoner et al. |

FOREIGN PATENT DOCUMENTS

| EP | 0966458 B1 | 8/2003 |
| WO | 99/15517 | 4/1999 |
| WO | 00/17650 | 3/2000 |
| WO | 2005/003086 | 1/2005 |

OTHER PUBLICATIONS

European Search Report issued regarding European Application No. 08250265.9 (Jun. 20, 2008).

Primary Examiner—Bernard Dentz
(74) Attorney, Agent, or Firm—Thompson Hine LLP

(57) ABSTRACT

Compounds having the general of formula I and/or formula II

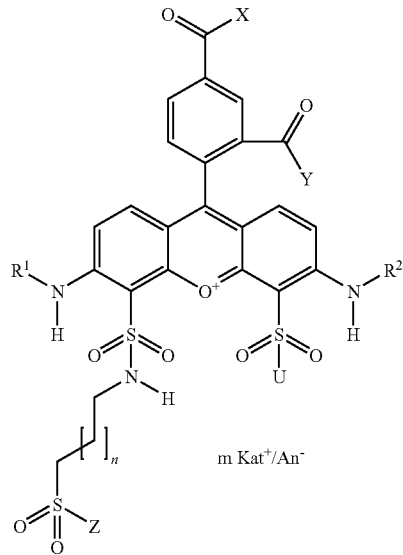

I

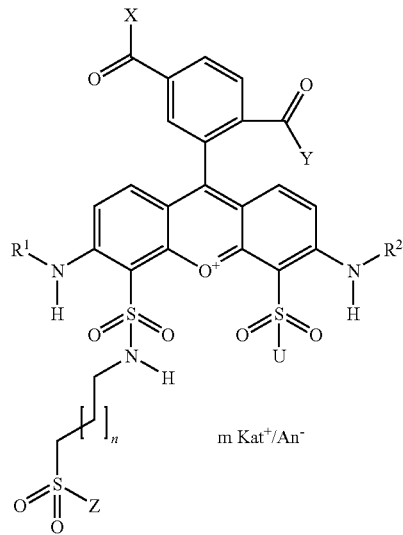

II wherein $R^1$ and $R^2$ are the same or different and are independently selected from the group consisting of —H, —$C_1$-$C_{18}$-alkyl or -ω-sulfoalkyl;

X and Y are the same or different and are independently selected from the group consisting of —O⁻, —OH, —SH, —NH—$NH_2$, —F, —Cl, —Br, —I, —O-Su (succinimidyl/sulfosuccinimidyl), —O-STP (4-sulfo-2,3,5,6-tetrafluorophenyl), —O-TFP (2,3,5,6-tetrafluorophenyl), —O-benzotriazole, -benzotriazole, —NR—CO—$CH_2$—I, —$NR_2$, —NR-biomolecule, —NR-L-COO⁻, —NR-L-COOH, —NR-L-COO-Su, —NR-L-COO- STP, —NR-L-COO-TFP, —NR-L-CONR$_2$, —NR-L-CO-biomolecule, —NR-L-CO—NH—NH$_2$, —NR-L-OH, —NR-L-O-phosphoramidite, —NR-L-CHO, —NR-L-maleimid, or —NR-L-NH—CO—CH$_2$—I; where R is equal to R$^1$ and R$^2$ and L is selected from the group consisting of a divalent linear (—(CH$_2$)$_o$—, o=1 to 15), crossed, or cyclic alkane group that can be substituted by at least one atom selected from the group consisting of oxygen, substituted nitrogen, and/or sulfur, and the biomolecule is a protein, antibody, nucleotide, oligonucleotide, biotin, or hapten;

Z is —O$^-$ or OH;

U is —O$^-$, —OH, or NH-L-SO$_2$Z;

Kat is Li, Na, K, ammonium (mono-, di- or trialkyl) or another cation;

An is F, Cl, Br, I, BF$_4$, ClO$_4$, CH$_3$CO$_2$, CF$_3$CO$_2$ or another anion;

m is an integer from 1-6 necessary to compensate the negative or positive charge from the dye moiety in formula I or formula II; and n is an integer from 0-12;

compositions containing these compounds, and methods using these compounds, are disclosed.

14 Claims, 4 Drawing Sheets

SULFONAMIDE DERIVATIVES OF XANTHENE COMPOUNDS

TECHNICAL FIELD

Compounds, compositions, and methods using sulfonamide derivates of fluorescent xanthene compounds.

BACKGROUND

Organic fluorescent compounds, also referred to as dyes, are used as sensitive detection reagents in biological assays. Xanthene-type dyes are commercially available as research reagents from a number of manufacturers.

Fluorescein derivatives of these compounds are based on the 3H-xanthene-6-ol-3-one core structure, with a 2-carboxyphenyl group at C9 of the central ring. Rhodamine dyes typically have a 6-amino-3H-xanthene-3-imine core structure with the same 2-carboxyphenyl group at C9. Rhodol based dyes have a central 6-amino-3H-xanthene-3-one structure with the same 2-carboxyphenyl group at C9.

Adding negatively charged sulfonate groups to fluorescent dyes increases their water solubility, facilitating use in biological applications and reducing dye-dye interactions due to like charge repulsion. Sulfonation has been used to modify cyanine dyes (U.S. Pat. Nos. 5,268,486; 5,486,616; 5,569,587; and 5,569,766) and xanthene-type dyes (U.S. Pat. No. 6,130,101).

Additional compounds, compositions, and methods are desirable.

BRIEF DESCRIPTION OF THE DRAWINGS

This application contains at least one drawing executed in color. A Petition under 37 C.F.R. §1.84 requesting acceptance of the color drawings is filed separately on even date herewith. Copies of this patent or patent application publication with color drawing(s) will be provided by the Office upon request and payment of the necessary fee.

DETAILED DESCRIPTION

Figure 1:
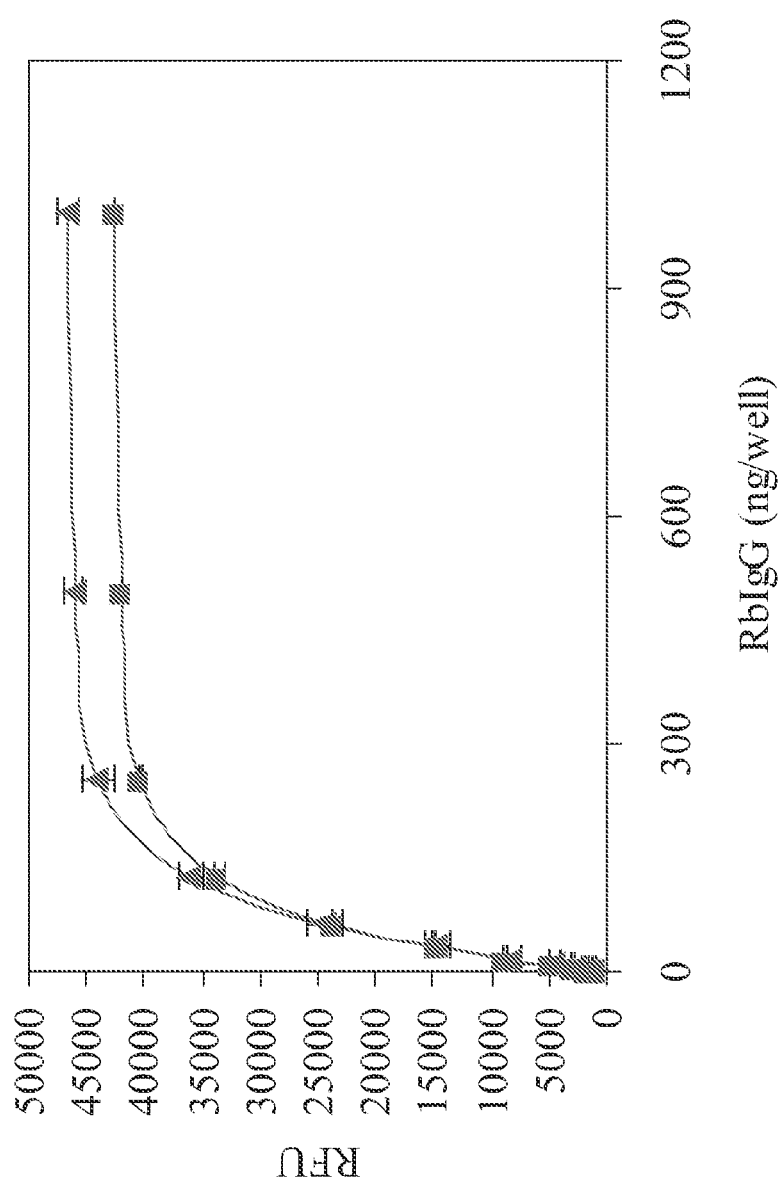
FIG. 1 illustrates use of one specific compound (formula V) as a Goat-Anti-Rabbit conjugate used in a protein assay (formula V-GAR conjugate).

Sulfonamide derivates, particularly aryl sulfonamide derivatives, of compounds containing a xanthene ring structure, are disclosed. These are referred to as fluorescent xanthene compounds or dyes, and include fluoresceins, rhodol dyes, rhodamines, and their reactive derivatives and conjugates. Addition of one or more aryl sulfonamide derivates and hydrophilic constituents to the sulfonamide nitrogen results in enhanced hydrophilicity and other properties over those of unsubstituted compounds. In one embodiment, the compounds optionally contain a reactive group that may be used for covalent coupling to biomolecules.

These compounds have enhanced fluorescence, water solubility, and biocompatibility, and may be used in compositions and methods as fluorescent probes in biological and other types of assays. Their properties compare favorably with negatively charged sulfonate derivates.

One embodiment includes xanthene dye derivatives that contain, in addition to the sulfonamide derivative, at least one reactive group L-Rt where L is a linker group covalently attached to the dye and Rt is a reactive group that is capable of covalently linking to another molecule.

One embodiment is at least one compound of general formula I or general formula II

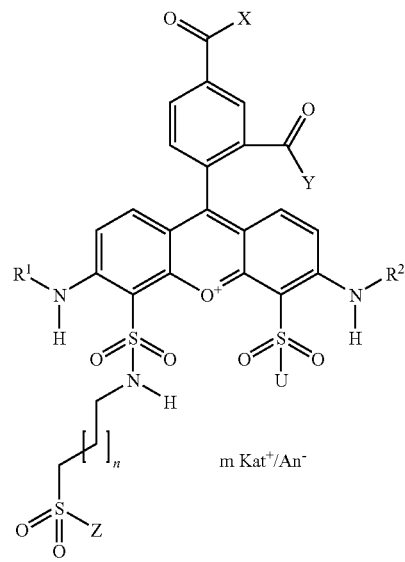

I

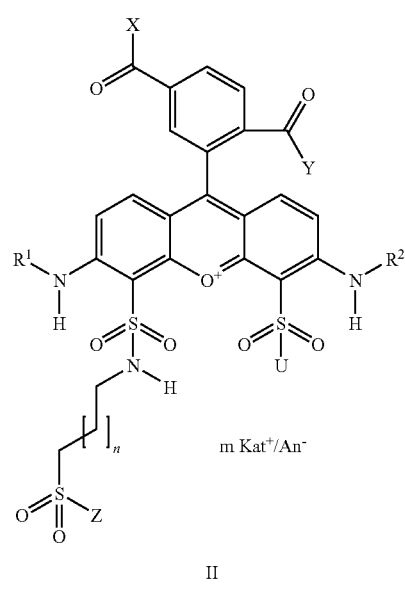

II wherein $R^1$ and $R^2$ are the same or different and are independently selected from the group consisting of —H, —$C_1$-$C_{18}$-alkyl or -ω-sulfoalkyl;

X and Y are the same or different and are independently selected from the group consisting of —O⁻, —OH, —SH, —NH—NH₂, —F, —Cl, —Br, —I, —O-Su (succinimidyl/sulfosuccinimidyl), —O-STP (4-sulfo-2,3,5,6-tetrafluorophenyl), —O-TFP (2,3,5,6-tetrafluorophenyl), —O-benzotriazole, -benzotriazole, —NR—CO—CH₂—I, —NR₂, —NR-biomolecule, —NR-L-COO⁻, —NR-L-COOH, —NR-L-COO-Su, —NR-L-COO-STP, —NR-L-COO-TFP, —NR-L-CONR₂, —NR-L-CO-biomolecule, —NR-L-CO—NH—NH₂, —NR-L-OH, —NR-L-O-phosphoramidite, —NR-L-CHO, —NR-L-maleimid, or —NR-L-NH—CO—CH₂—I; where R is equal to R¹ and R² and L is selected from the group consisting of a divalent linear (—(CH₂)ₒ—, o=1 to 15), crossed, or cyclic alkane group that can be substituted by at least one atom selected from the group consisting of oxygen, substituted nitrogen, and/or sulfur, and the biomolecule is a protein, antibody, nucleotide, oligonucleotide, biotin, or hapten;

Z is —O⁻ or OH;

U is —O⁻, —OH, or NH-L-SO₂Z;

Kat is Li, Na, K, ammonium (mono-, di- or trialkyl) or another cation;

An is F, Cl, Br, I, BF₄, ClO₄, CH₃CO₂, CF₃CO₂ or another anion;

m is an integer from 1-6 necessary to compensate the negative or positive charge from the dye moiety in formula I or formula II; and n is an integer from 0-12.

In embodiments, compounds of the general formula I and/or formula II include embodiments of formula III (V03-04093), formula IV, formula V (V03-04115), formula VI, formula VII (V03-04153), formula VIII, formula IX (V02-06158), formula X, formula XI (V03-04118), formula XII, formula XIII (V03-04120), formula XIV, formula XV (V03-04133), and/or formula XVI, as follows:

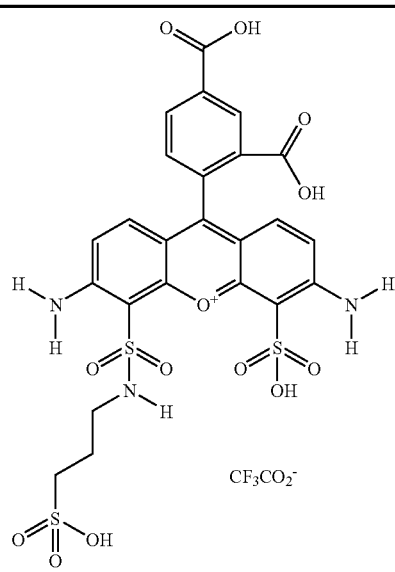

III (V03-04093)

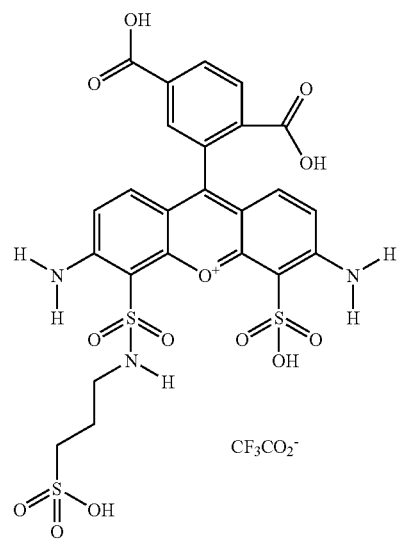

IV

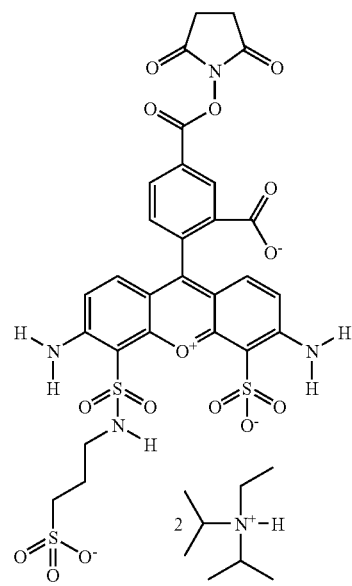

V (V03-04115)

-continued
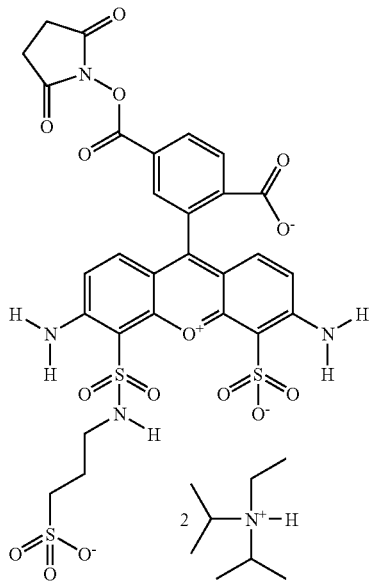
VI
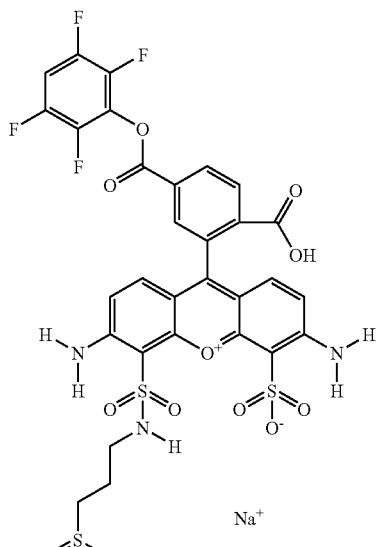
VIII
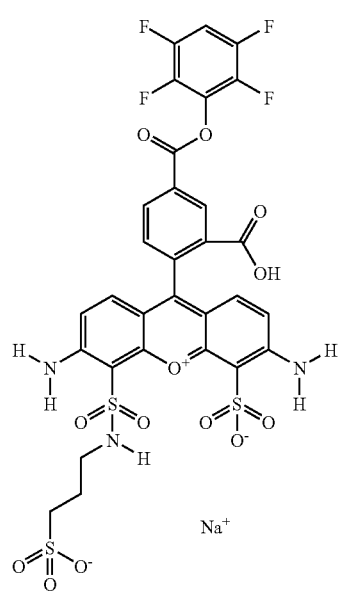
VII (V03-04153)
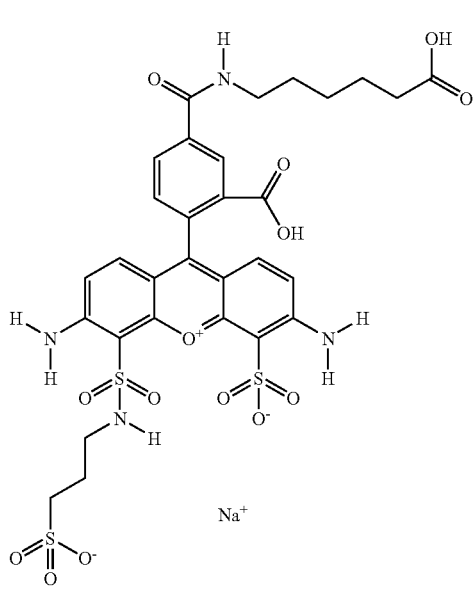
IX (V02-06158)

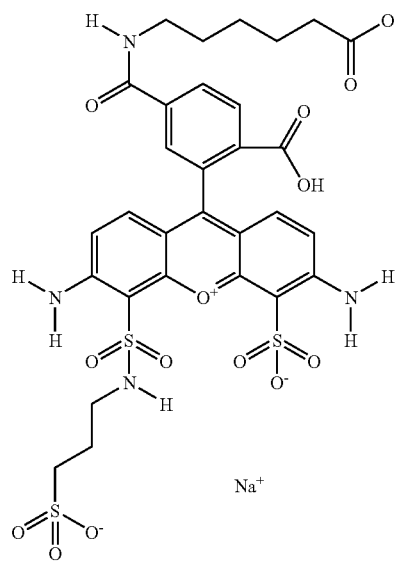
X
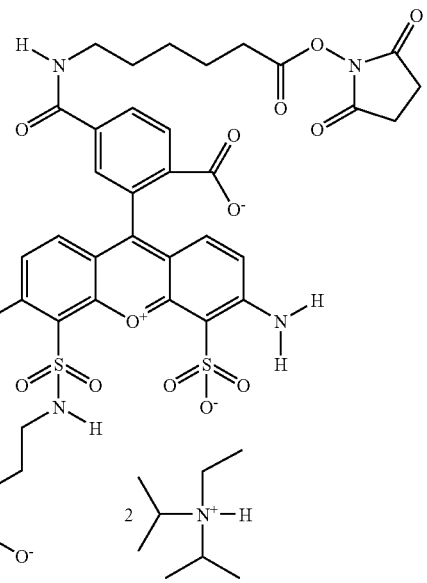
XII
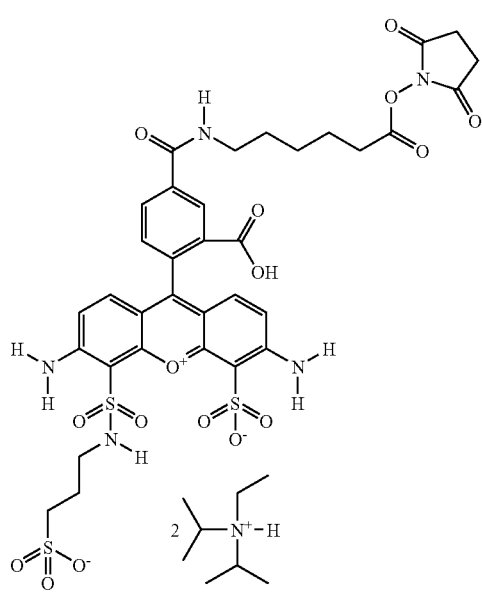
XI (V03-04118)
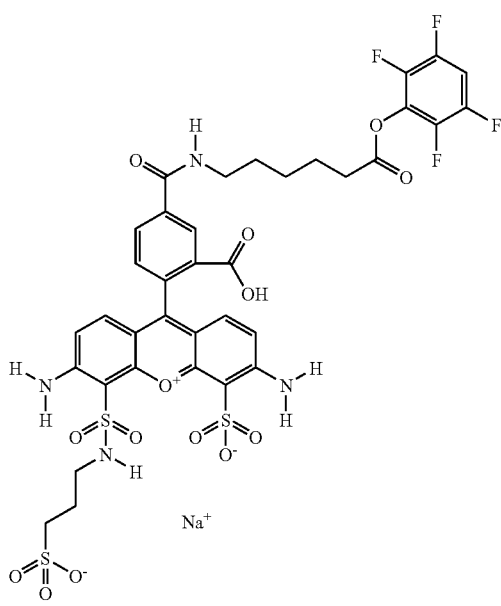
XIII (V03-04120)

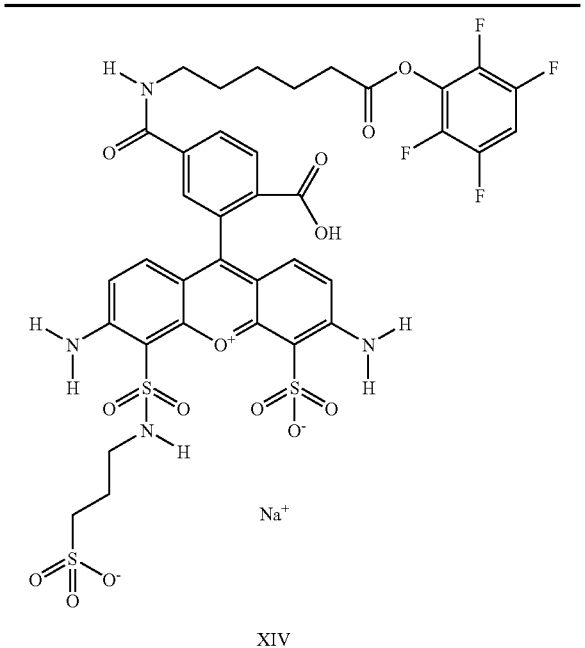
XIV
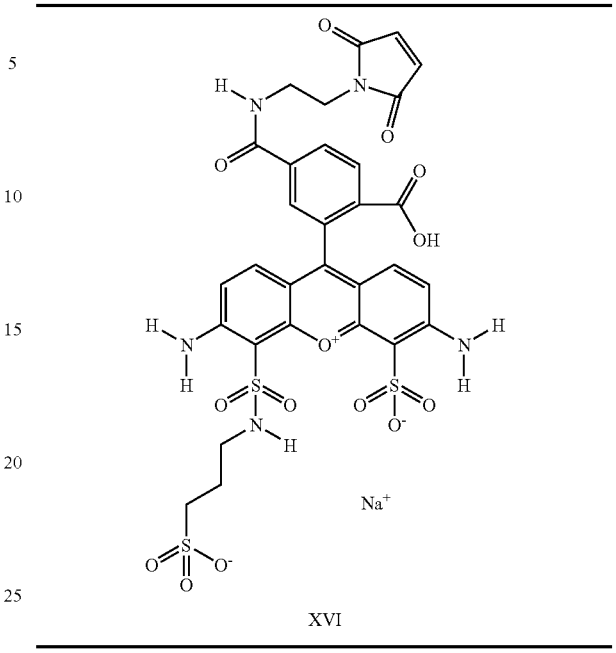
XVI
Another embodiment is a biocompatible dye composition comprising at least one excipient and at least one compound of general formula I or general formula II
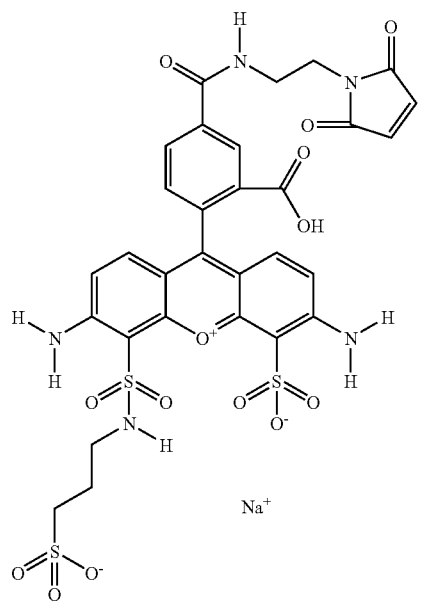
XV (V03-04133)
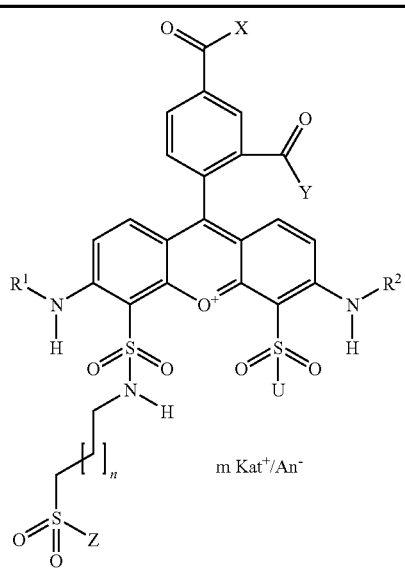
I

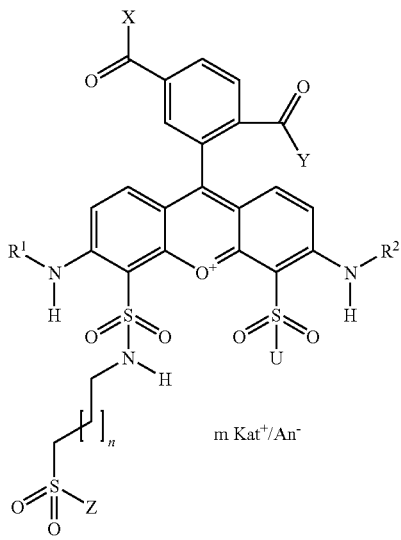

II wherein

R¹ and R² are the same or different and are independently selected from the group consisting of —H, —$C_1$-$C_{18}$-alkyl or -ω-sulfoalkyl;

X and Y are the same or different and are independently selected from the group consisting of —O⁻, —OH, —SH, —NH—$NH_2$, —F, —Cl, —Br, —I, —O-Su (succinimidyl/sulfosuccinimidyl), —O-STP (4-sulfo-2,3,5,6-tetrafluorophenyl), —O-TFP (2,3,5,6-tetrafluorophenyl), —O-benzotriazole, -benzotriazole, —NR—CO—$CH_2$—I, —$NR_2$, —NR-biomolecule, —NR-L-COO⁻, —NR-L-COOH, —NR-L-COO-Su, —NR-L-COO-STP, —NR-L-COO-TFP, —NR-L-$CONR_2$, —NR-L-CO-biomolecule, —NR-L-CO—NH—$NH_2$, —NR-L-OH, —NR-L-O-phosphoramidite, —NR-L-CHO, —NR-L-maleimid, or —NR-L-NH—CO—$CH_2$—I; where R is equal to R¹ and R² and L is selected from the group consisting of a divalent linear (—$(CH_2)_o$—, o=1 to 15), crossed, or cyclic alkane group that can be substituted by at least one atom selected from the group consisting of oxygen, substituted nitrogen, and/or sulfur, and the biomolecule is a protein, antibody, nucleotide, oligonucleotide, biotin, or hapten;

Z is —O⁻ or OH;

U is —O⁻, —OH or NH-L-$SO_2$Z;

Kat is Li, Na, K, ammonium (mono-, di- or trialkyl) or another cation;

An is F, Cl, Br, I, $BF_4$, $ClO_4$, $CH_3CO_2$, $CF_3CO_2$ or another anion;

m is an integer from 1-6 necessary to compensate the negative or positive charge from the dye moiety in formula I or formula II; and n is an integer from 0-12.

Another embodiment is a biocompatible dye composition comprising at least one excipient and a compound selected from the group consisting of formula III, formula IV, formula V, formula VI, formula VII, formula VIII, formula IX, formula X, formula XI, formula XII, formula XIII, formula XIV, formula XV, formula XVI, and combinations thereof, wherein formulas III-XVI are as previously described.

Another embodiment is a method of labelling at least one biomolecule, the method comprising providing a composition comprising at least one excipient and at least one compound of general formula I or general formula II

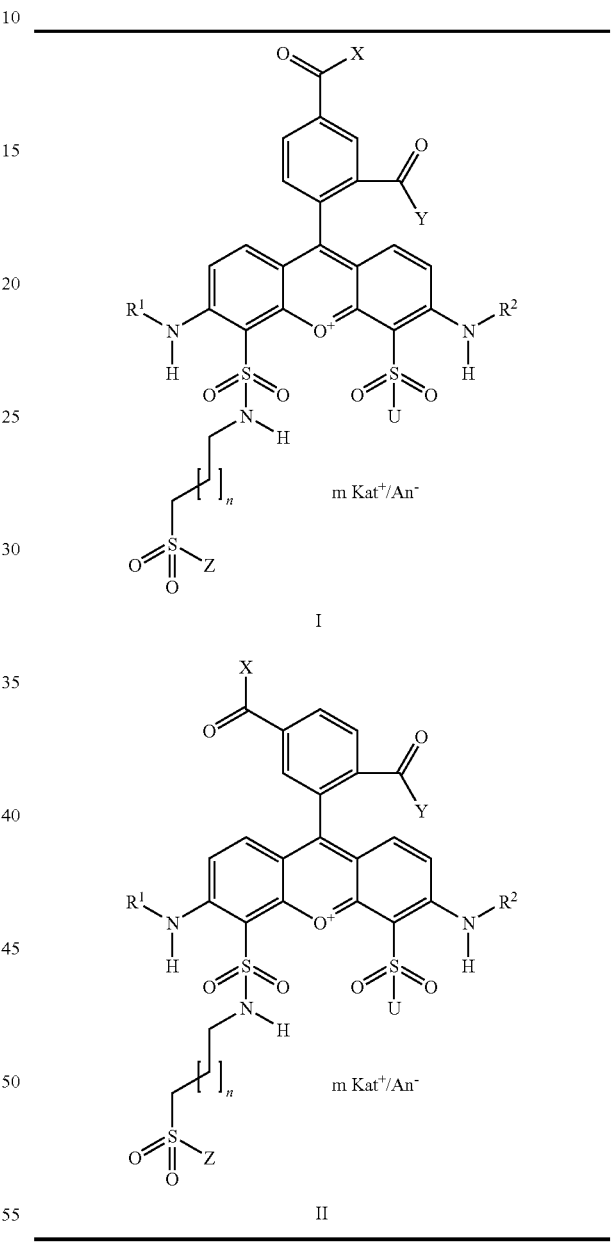

in an effective concentration to a biomolecule under conditions sufficient for binding the compound to the biomolecule, and detecting the biomolecule-bound compound, wherein R¹ and R² are the same or different and are independently selected from the group consisting of —H, —$C_1$-$C_{18}$-alkyl or -ω-sulfoalkyl;

X and Y are the same or different and are independently selected from the group consisting of —O⁻, —OH, —SH, —NH—NH$_2$, —F, —Cl, —Br, —I, —O-Su (succinimidyl/sulfosuccinimidyl), —O-STP (4-sulfo-2,3,5,6-tetrafluorophenyl), —O-TFP (2,3,5,6-tetrafluorophenyl), —O-benzotriazole, -benzotriazole, —NR—CO—CH$_2$—I, —NR$_2$, —NR-biomolecule, —NR-L-COO$^-$, —NR-L-COOH, —NR-L-COO-Su, —NR-L-COO-STP, —NR-L-COO-TFP, —NR-L-CONR$_2$, —NR-L-CO-biomolecule, —NR-L-CO—NH—NH$_2$, —NR-L-OH, —NR-L-O-phosphoramidite, —NR-L-CHO, —NR-L-maleimid, or —NR-L-NH—CO—CH$_2$—I; where R is equal to R$^1$ and R$^2$ and L is selected from the group consisting of a divalent linear (—(CH$_2$)$_o$—, o=1 to 15), crossed, or cyclic alkane group that can be substituted by at least one atom selected from the group consisting of oxygen, substituted nitrogen, and/or sulfur, and the biomolecule is a protein, antibody, nucleotide, oligonucleotide, biotin, or hapten;

Z is —O$^-$ or OH;

U is —O$^-$, —OH or NH-L-SO$_2$Z;

Kat is Li, Na, K, ammonium (mono-, di- or trialkyl) or another cation;

An is F, Cl, Br, I, BF$_4$, ClO$_4$, CH$_3$CO$_2$, CF$_3$CO$_2$ or another anion;

m is an integer from 1-6 necessary to compensate the negative or positive charge from the dye moiety in formula I or formula II; and n is an integer from 0-12.

Another embodiment is a method of labelling at least one biomolecule, the method comprising providing a composition comprising at least one excipient and a compound of at least one of formula III, formula IV, formula V, formula VI, formula VII, formula VIII, formula IX, formula X, formula XI, formula XII, formula XIII, formula XIV, formula XV, formula XVI, and combinations thereof, in an effective concentration to a biomolecule under conditions sufficient for binding the compound to the biomolecule, and detecting the biomolecule-bound compound, wherein formulas III-XVI are as previously described.

In embodiments, compounds of the general formula I and/or formula II include embodiments of formula III (V03-04093), formula IV, formula V (V03-04115), formula VI, formula VII (V03-04153), formula VIII, formula IX (V02-06158), formula X, formula XI (V03-04118), formula XII, formula XIII (V03-04120), formula XIV, formula XV (V03-04133), and formula XVI.

In one embodiment, 5-carboxy-rhodamine 110 is formed as an isomeric mixture with 6-carboxy-rhodamine 110, using m-aminophenol and trimellitic acid anhydride as starting materials, as follows:

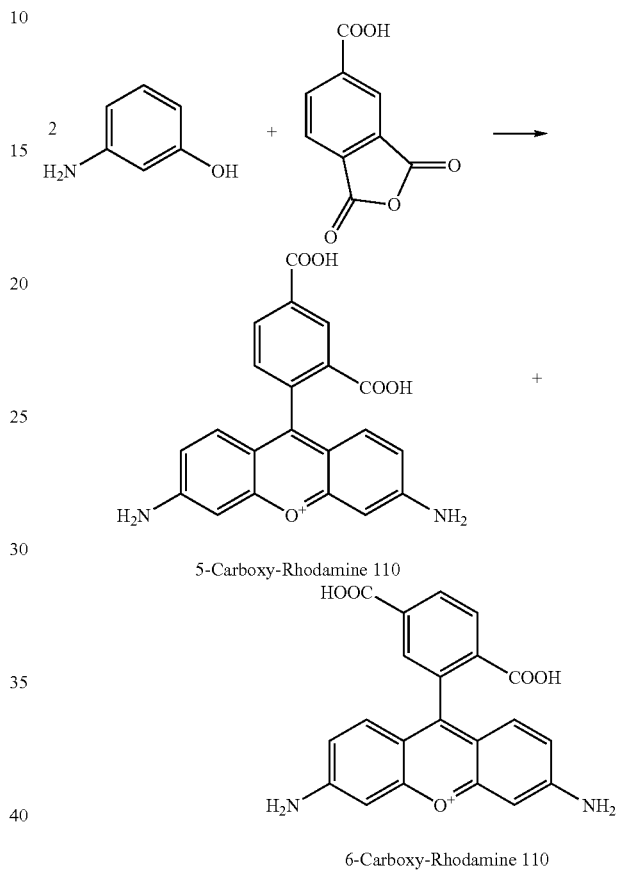

The yield of this 5/6-carboxy-rhodamine isomer mixture was about 16%.

Starting with 5-carboxy-rhodamine, the reaction proceeds via sulfochlorination as follows:

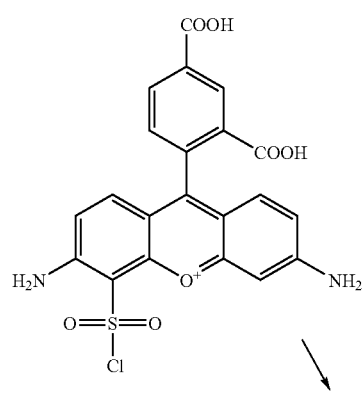

-continued

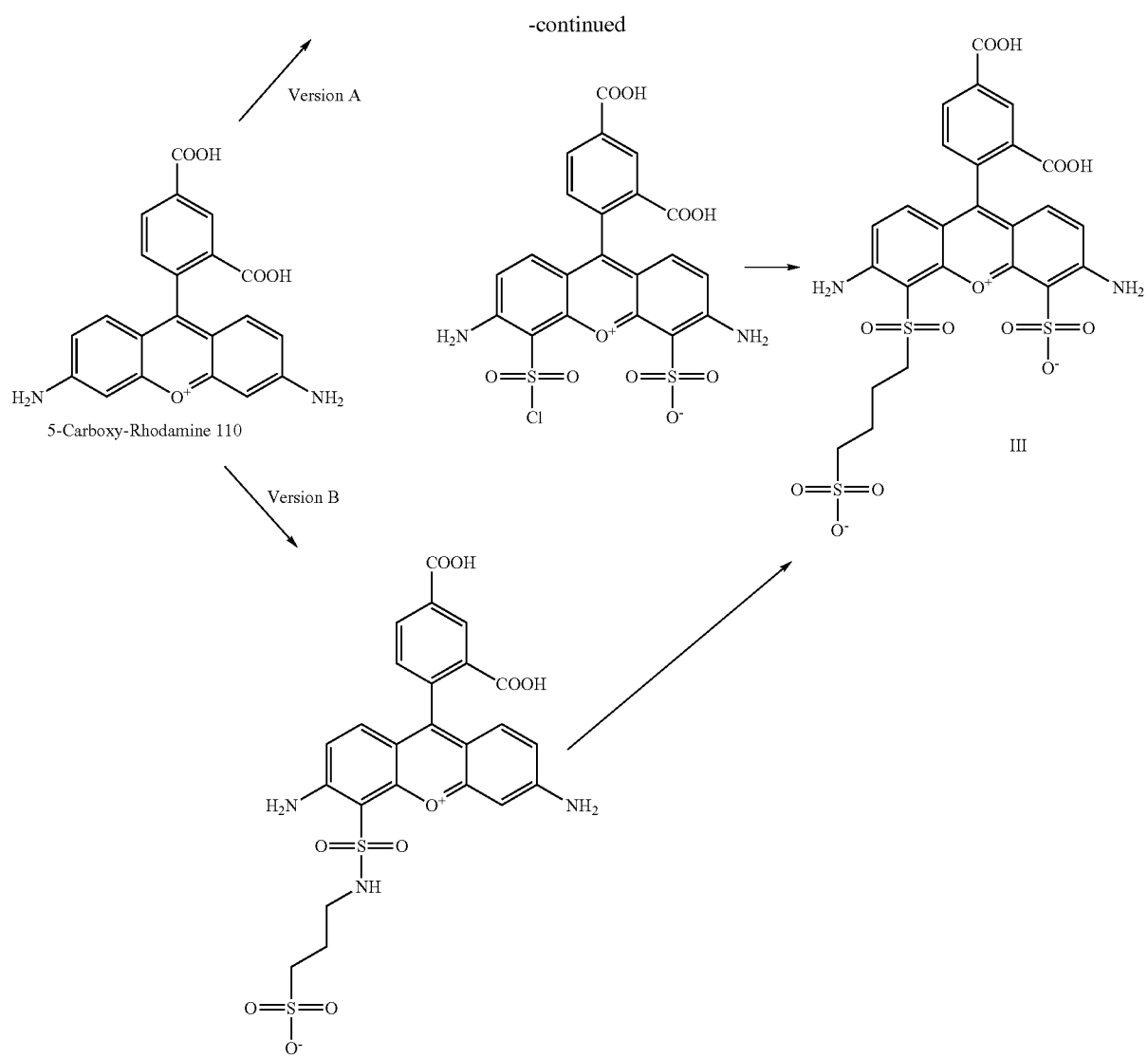

One embodiment uses sulfonamide xanthene dye derivatives as fluorescent stains. In this embodiment, the dye derivatives are used to stain a biomolecule (e.g., protein, etc.) in various applications (e.g., separated by electrophoresis on gels or blots, in cells, in tissue sections, etc.). In this embodiment, a reactive sulfonamide xanthene dye derivative may be covalently linked to the biomolecule, and/or constituents may be added to the dye derivative to promote non-covalent interaction (e.g., adsorption) of the dye derivative to the biomolecule. Such non-covalent interactions may be facilitated by adding hydrophobic constituents (e.g., alkyl chains, aromatic rings, etc.) that lack polar or charged group. In one embodiment, a combination of hydrophobic constituents and charged or polar hydrophilic constituents on another part of the dye compound promote adsorption staining of biomolecules such as proteins.

The compounds are photostable green fluorophores have an absorbance maximum that is a good intermediate wavelength that enhances the laser line and hence facilitates detection of compounds in a sample using an argon ion laser. The compounds may be used as the only dye in a sample. Alternatively, the compounds may be used in multiplexing assays.

One embodiment uses the compounds in multiplexing assays in combination with a red dye. One embodiment uses the compounds in immunofluorescence microscopy. One embodiment uses the compounds in High Content Analysis (HCA) assays and compound screening (e.g., using various stimulators to quantify protein cytoplasm to nuclear translocation, protein induction, etc.). One embodiment uses the compounds in immunofluorescence (direct and indirect) (e.g., to detect and quantify localization of intracellular targets). One embodiment uses the conjugated compounds as stand alone primary antibodies. One embodiment incorporates the compounds in a turnkey reagent kit for HCA assays.

The invention will be further appreciated with respect to the following Examples.

Example 1

Synthesis of Compound III (V03-04093)
Via Version A

A solution of 821 mg (2 mmol) 5-(6)-Carboxyrhodamine 110, hydrochloride (either pure isomers or mixture) in 10 ml chlorosulfonic acid was heated to 80° C. for one hour. After cooling to room temperature, 10 ml 20% fuming sulphuric acid was added and the solution was kept at room temperature for 90 minutes. The solution was then poured carefully on 400 g crushed ice and the resulting precipitate was filtered off. After washing with ice water, the precipitate was dissolved in a solution of 238 mg (2 mmol) 3-aminopropanesulfonic acid in a mixture of acetonitrile and water (10 ml; V/V=1:1) containing 1 ml triethylamine. After removing the solvents, the residue was purified by column chromatography (RP-18 silica gel; acetonitrile/water 2/8 containing 1% trifluoroacetic acid).

UV-Vis (pH 7 buffer): $\lambda_{abs}$=491 nm
MS (ESI+) [m/z]: 656.4 [M]+

Example 2

Synthesis of Compound V (V03-04115)

V03-04093 (154 mg; 0.2 mmol) was dissolved in a mixture of DMF and water (10 ml; V/V=3:1) and cooled to 0° C. To this solution O-succinimidyl-N,N,N',N'-tetramethyluronium tetrafluoroborate (120 mg; 0.4 mmol) and diisopropylethylamine (52 mg; 0.4 mmol) were added. After 20 minutes at 0° C., the solvents were distilled off in high vacuum. The residue was purified by column chromatography (RP-18 silica gel; acetonitrile/water 2/8).

UV-Vis (pH 7 buffer): $\lambda_{abs}$=494 nm
MS (ESI−) [m/z]: 751.1 [M+H]−

Example 3

Synthesis of Compound VII (V03-04153)

V03-04093 (154 mg; 0.2 mmol) was dissolved in a mixture of DMF and water (10 ml; V/V=3:1). To this solution tetrafluorophenol (33 mg; 0.2 mmol), N,N'-dicyclohexylcarbodiimide (82 mg; 0.4 mmol) and diisopropylethylamine (52 mg; 0.4 mmol) were added. After 24 hours at room temperature, the solvents were distilled off in high vacuum. The residue was dissolved in 10 ml water containing sodium chloride (584 mg; 10 mmol) and purified by column chromatography (RP-18 silica gel; acetonitrile/water 2/8).

UV-Vis (pH 7 buffer): $\lambda_{abs}$=495 nm
MS (ESI−) [m/z]: 802.1 [M]−

Example 4

Synthesis of Compound IX (V02-06158)

Compound V (V03-04115) (prepared according to Example 2) (101 mg; 0.1 mmol) was dissolved in a mixture of DMF and water (5 ml; V/V=3:1). To this solution aminocaproic acid (26 mg; 0.2 mmol) and diisopropylethylamine (52 mg; 0.4 mmol) were added. After two hours at room temperature, the solvents were distilled off in high vacuum. The residue was dissolved in 10 ml water containing sodium chloride (584 mg; 10 mmol) and purified by column chromatography (RP-18 silica gel; acetonitrile/water 3/7).

UV-Vis (pH 7 buffer): $\lambda_{abs}$=492 nm
MS (ESI−) [m/z]: 767.1 [M]−

Example 5

Synthesis of Compound XI (V03-04118)

Compound XI (V03-04118) was prepared analogously to Compound V (V03-04115) in Example 2 with Compound IX (V02-06158) (79 mg; 0.1 mmol) as the starting material.

UV-Vis (pH 7 buffer): $\lambda_{abs}$=492 nm
MS (ESI−) [m/z]: 864.1 [M+H]−

Example 6

Synthesis of Compound XII (V03-04120)

Compound XII (V03-04120) was prepared analogously to Compound VII (V03-04153) in Example 3 with Compound IX (79 mg; 0.1 mmol) as the starting material.

UV-Vis (pH 7 buffer): $\lambda_{abs}$=493 nm
MS (ESI−) [m/z]: 915.2 [M]−

Example 7

Synthesis of Compound XV (V03-04133)

Compound V (V03-04115) (prepared according to Example 2) (101 mg; 0.1 mmol) was dissolved in a mixture of DMF and water (5 ml; V/V=3:1). To this solution 2-maleimidoethylamine trifluoroacetate (38 mg; 0.15 mmol) and diisopropylethylamine (52 mg; 0.4 mmol) were added. After two hours at room temperature, the solvents were distilled off in high vacuum. The residue was dissolved in water containing sodium chloride (584 mg; 10 mmol) and purified by column chromatography (RP-18 silica gel; acetonitrile/water 3/7).

UV-Vis (pH 7 buffer): $\lambda_{abs}$=493 nm
MS (ESI−) [m/z]: 776.1 [M]−

Example 8

Conjugation to Proteins

Compounds were rendered reactive by adding groups enabling them to covalently link to other molecules. Reactive compounds were conjugated to macromolecules such as proteins (e.g., antibodies, Streptavidin) and used in immunofluorescence assays (e.g. Western blot, ELISA, flow cytometry, in-cell assays, etc).

Three×10 mg goat anti-rabbit IgG (H+L) (GAR) and 3×10 mg goat anti-mouse IgG (H+L) (GAM) at 10 mg/ml were dialyzed overnight against five liters of 50 mM borate buffer, pH 8.4. Each of the dialyzed antibodies was labeled with 10 molar excess of each of the compounds of formulas V, XI and XII that had been reconstituted in 0.1 ml DMF. The reaction was carried out for two hours at room temperature (about 20° C. to about 22° C.). The excess unreacted compound was removed by dialyzing the samples overnight against 3×5 L 0.1 M sodium phosphate buffer, 0.15 M NaCl, pH 7.2 (phosphate buffered saline (PBS)). Three changes of PBS were used. Upon making a 1:100 dilution of the labeled proteins and performing absorbance scans of the samples, mole dye to mole protein ratios of between 5 and 6 (inclusive) was determined for conjugates made with compounds of each of formulas V, XI, and XIII.

Three×10 mg streptavidin (SA) at 10 mg/ml was reconstituted in 50 mM borate buffer, pH 8.4. The streptavidin was labeled with a five molar excess of each of the compounds of formulas V, XI, and XIII that had been reconstituted in 0.1 ml DMF. The reaction was carried out for two hours at room temperature. The excess unreacted compound was removed by dialyzing the sample overnight against 3×5 L of 0.1 M sodium phosphate buffer, 0.15 M NaCl, pH 7.2 (PBS). Three changes of PBS were used. Upon making a 1:100 dilution of the labeled proteins and performing absorbance scans of the samples, mole dye to mole protein ratios of between 2 and 4

(inclusive) was determined for conjugates made of compounds of each of formulas V, XI, and XII.

One×10 mg NeutrAvidin® Biotin Binding Protein (NA) (Pierce Biotechnology, Inc.) at 10 mg/ml was reconstituted in 50 mM borate buffer, pH 8.4. NeutrAvidin® Biotin Binding Protein was labeled with a five molar excess of the compound of formula V had been reconstituted in DMF. The reaction was carried out for two hours at room temperature. The excess unreacted compound was removed by dialyzing the sample overnight against 3×5 L of 0.1 M sodium phosphate buffer, 0.15 M NaCl, pH 7.2 (PBS). Three changes of PBS were used. Upon making a 1:100 dilution of the labeled protein and performing absorbance scans of the samples, a mole dye to mole protein ratio of between 2 and 3 (inclusive) was determined for the conjugate made with the compound.

Example 9

Plate Assay of Goat Anti-Rabbit Conjugates

Data for a functional assay using the compound of formula V-Goat anti-Rabbit (GAR) conjugate are shown in FIG. 1. The assay was performed at room temperature (about 20° C. to about 22° C.) on a serially diluted 96-well white opaque Rabbit IgG-coated plate (10 µg/ml to 0 µg/ml). The plate was washed 3×200 µl with PBS-0.05% Tween and 1×200 µl with PBS buffer. The formula V-GAR conjugate was diluted to 0.004 mg/ml in PBS buffer. The diluted conjugate was applied to wells of the plates (100 µl/well), the plate was incubated for one hour, and then washed as described above. PBS buffer was added to the plate (100 µl/well) and the fluorescent intensity was captured using the TECAN Safire® at green laser setting, with an excitation wavelength of 495 nm and an emission wavelength of 519 nm. Commercially available Alexa Fluor® 488-GAR (Molecular Probes, Eugene Oreg.) was diluted to the same concentration and evaluated as previously described with reference to the formula V-GAR conjugate.

As shown in FIG. 1, Rabbit IgG was detected at a level of 2 ng/well with the formula V-GAR conjugate. When a formula III-GAR conjugate was assayed, there was 10% higher signal intensity than the Alexa Fluor® 488-GAR conjugate (data not shown).

Example 10

Plate Assay Using Streptavidin and NeutrAvidin® Conjugates

Figure 2:
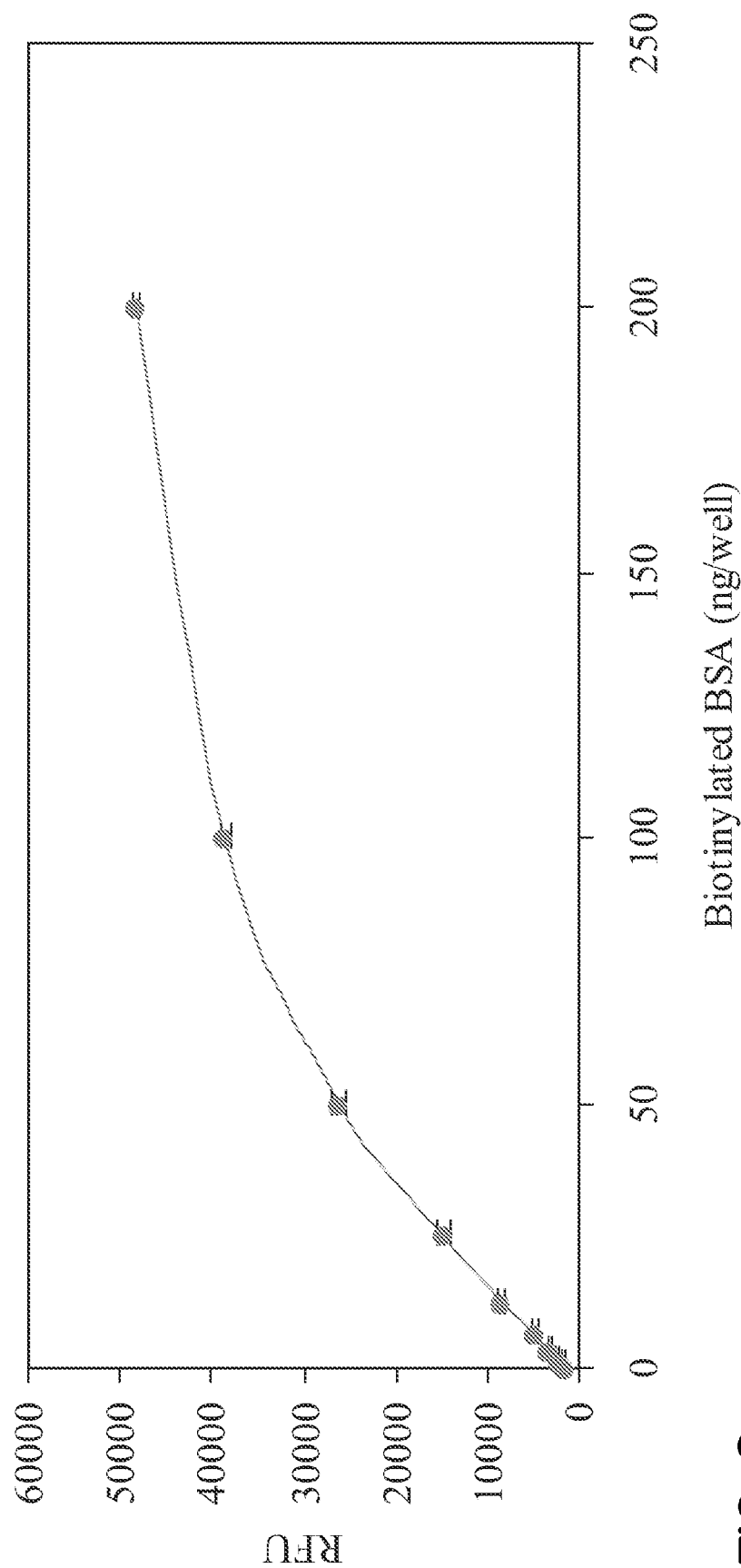
FIG. 2 illustrates use formula V as a Streptavadin conjugate.
Figure 3:
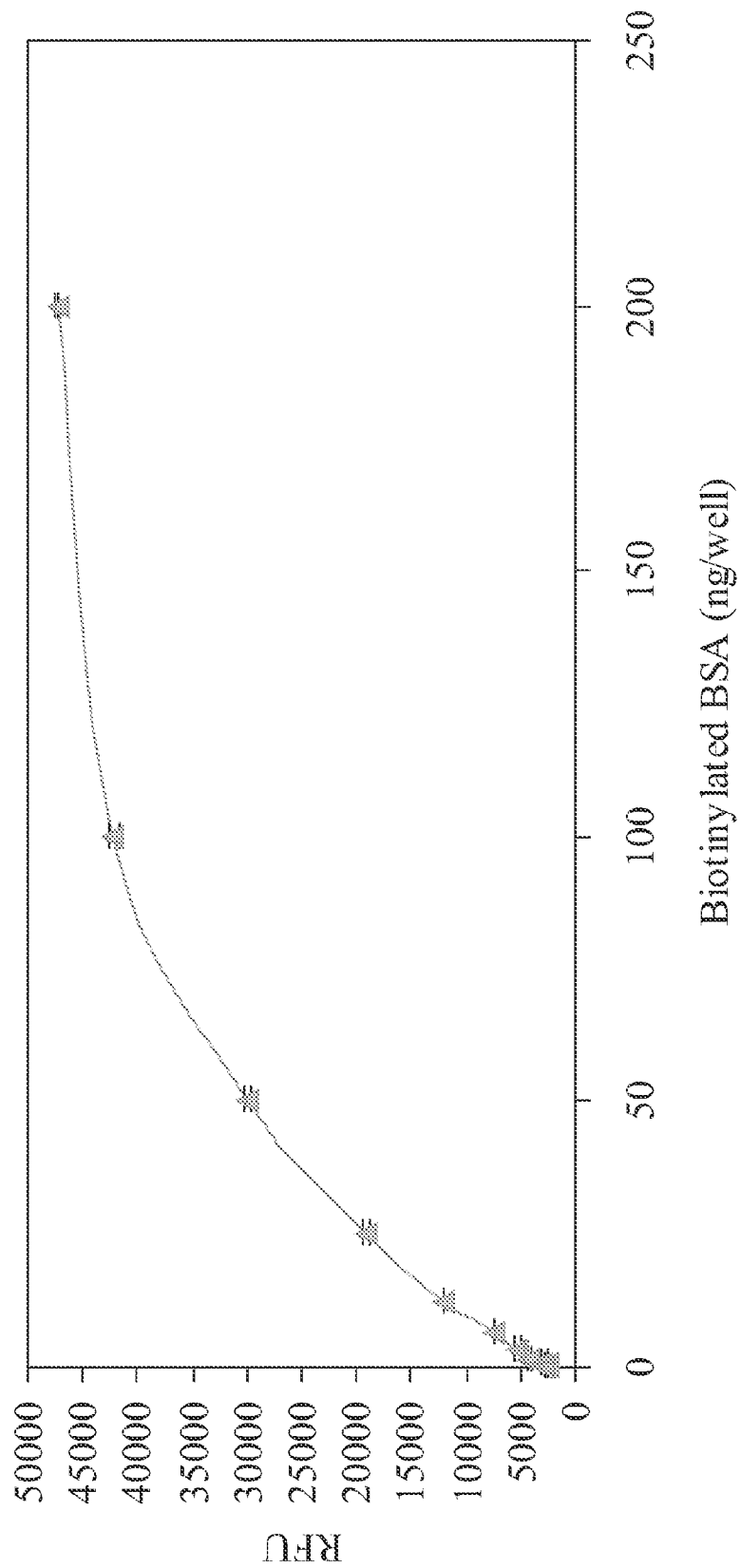
FIG. 3 illustrates use of formula V as a NeutrAvadin® conjugate.

Data for functional assays using the compound of formula V conjugated each of Streptavidin and NeutrAvidin® are shown in FIGS. 2 and 3, respectively. The assays were performed on serially diluted 96-well white opaque Biotinylated-BSA coated plates (2 µg/ml to 0 µg/ml). The plates were washed 3×200 µl with PBS-0.05% Tween and 1×200 µl with PBS buffer. Formula V-Streptavidin (SA) and Formula V-NeutrAvidin® (NA) conjugates were diluted 0.004 mg/ml in PBS buffer. Diluted conjugates were applied to the wells of the plates (100 µl/well), the plates were covered and protected from light, incubated for one hour, then washed as previously described. PBS buffer was added to the plates (100 µl/well) and the fluorescent intensity was captured using the TECAN Safire® at green laser setting. Commercially available Alexa Fluor® 488-SA (Molecular Probes) was diluted to the same concentration and evaluated as previously described with reference to the formula V conjugated SA.

As shown in FIG. 2 with reference to SA, and in FIG. 3 with reference to NA, with this assay biotinylated BSA was detected at a level of 2 ng/well with both Formula V conjugated Streptavidin and Formula V conjugated NeutrAvidin.

Example 11

Multiplex Western Blotting

A combination of recombinant mouse TNFα and Hela cell lysate were separated by electrophoresis on a 4-20% Tris-Glycine gel. The proteins were transferred to Hybond-LFP membrane (Amersham) and blocked overnight in 1×BSA/PBS-0.05% Tween. The blot was co-incubated for one hour with Mouse Anti-Tubulin MAb primary antibody (1 µg/ml) and Bovine Anti-TNFα primary antibody (1 µg/ml) diluted in PBS-0.05% Tween-20. Following incubation, the blot was washed 3×10 min with PBS-0.05% Tween-20. Secondary antibody-formula V-Goat-Anti-Rabbit (GAR) conjugates (0.067 µg/ml) and secondary antibody-DyLight™ 649-Goat-Anti-Mouse (GAM)-conjugates (0.067 µg/ml) diluted in PBS-0.05% Tween-20 were incubated to detect the protein. After this incubation, the blots were washed 6×5 min with PBS-0.05% Tween-20. The image was captured on a Typhoon 9410 Variable Mode Imager at green and red laser settings.

Figure 4:
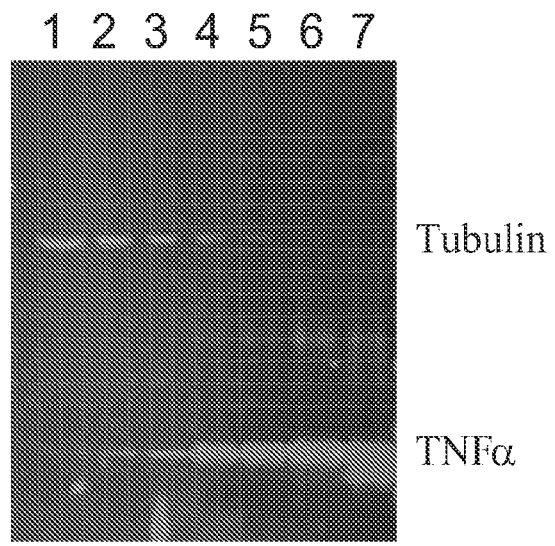
FIG. 4 shows use of formula V for protein detection by multiplex Western blotting.

Results are shown in FIG. 4. Each of lanes 1-7 contains the following amounts of recombinant mouse TNFα respectively: 0.20 ng, 0.39 ng, 0.78 ng, 6.25 ng, 12.5 ng, 25 ng, and 50 ng, and the following dilutions of HeLa cell lysate respectively: 1:1, 1:2, 1:4, 1:8, 1:16, 1:32 and 1:64 dilution of Hela Cell lysate. Bands stained red were TNFα (pure). Bands stained green were tubulin that was in the cell lysate. TNF α was detected down to 0.2 ng using formula V-GAR conjugates. The results demonstrated that the disclosed rhodamine conjugates may be used in multiplexing applications.

Example 12

Immunofluorescence Assay

A histologically prepared slide containing human small intestine normal tissue was deparraffinized by heating at 45° C. for 50 min in an incubator. The slide was rehydrated with two five-minute incubations in EZ-dewax solution and then washed once with ultrapure water and once with PBS-0.05% Tween-20 (PBST). The targets were retrieved by incubating the slide in Target Retrieval Solution at 95° C. to 99° C. for forty minutes, followed by cooling to room temperature for twenty minutes and rinsing once with PBS-0.05% Tween-20. The slide was washed 2×three minutes with PBS-0.05% Tween-20.

The slide was returned to its original incubation container, 15 ml of 3% Normal Goat Serum in PBS-0.05% Tween-20 was added, and the slide was incubated at 4° C. overnight. The slide was dried by centrifugation. Wheat Germ Agglutinin (WGA) conjugated to DyLight™ 680 was diluted to 10 µg/ml and rabbit anti-S100 primary antibody was diluted 1:400 (from the original concentration), both reagents were diluted in the same 1 ml of PBS-0.05% Tween-20. Two hundred µl of this working reagent was applied to the slide. The tissue contained on the slide was covered with an incubation chamber to prevent evaporation of the antibody solution. The slide was incubated for one hour with the primary antibodies. The slide was passively washed three times with PBS-0.05% Tween-20.

The Formula V-Goat Anti-Rabbit (GAR) conjugate was diluted to 10 μg/ml and 200 μl was applied to the slide. The tissue contained on the slide was covered with an incubation chamber to prevent evaporation of the antibody solution. The slide was incubated for one hour with the secondary antibody and then passively washed three times with PBS-0.05% Tween-20. The slide was dipped in PBS and then dried by centrifugation. One drop of fluorescence mounting medium was added to the slide followed by application of a cover slip. The slide was stored at 4° C. until visualization using a Zeiss confocal microscope.

Figure 5:
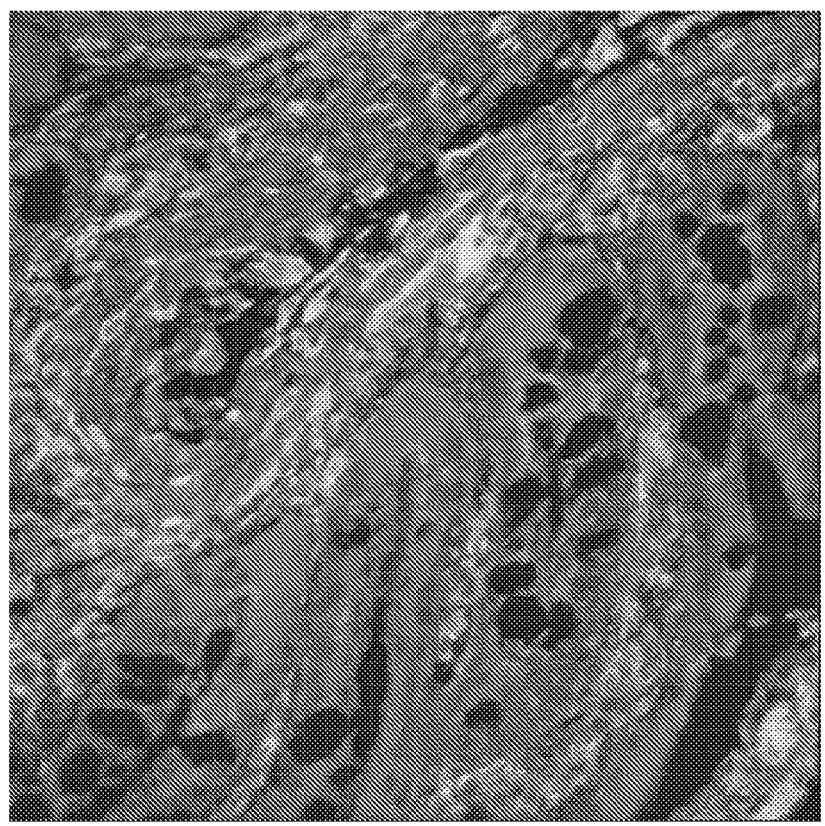
FIG. 5 shows use of formula V in immunofluorescence staining.

Results are shown in FIG. 5. Red staining areas indicate DyLight™ 680-WGA conjugates. Green staining areas indicate formula V-GAR conjugates. The results demonstrated that the disclosed rhodamine conjugates may be used in immunofluorescence applications Example 13

Fluorescence In-Situ Hybridization (FISH)

For cells with visible cytoplasm surrounding interphase and metaphase, slides are prepared by incubating the cells in 0.01 M HCl with 0.005% pepsin at 37° C. for ten minutes. The slides are then washed 2×1 minutes in PBS and incubated for ten minutes in 1% formaldehyde in PBS. The slides are incubated for 2×1 minute in PBS and then dehydrated in 70% ethanol for one minute, then at 95% ethanol for one minute, then at 100% ethanol for one minute, before air drying.

Ten μl of compound Formula V labeled probe for a target is dispensed into a 0.5 ml microcentrifuge tube and then incubated at 96° C. for five minutes in a water bath. The tubes are briefly centrifuged, then 10 μl of the probe mix is applied to the target and covered with a coverslip. The slides and probes are denatured for two minutes at 80° C. on a temperature controlled hot plate and then incubated for 12-18 h in a humidified environment at 37° C.

The coverslips are removed by soaking in 2×SSC/0.1% Tween-20 at 37° C. The slides are then washed 4×5 min in 0.5×SSC/0.1% SDS at 60° C. to 65° C., and then briefly rinsed with distilled water and air dried out of direct light. DAPI anti-fade solution (20 μl) is applied to the target and covered with a coverslip (24 mm×50 mm) before viewing on a fluorescent microscope equipped with the appropriate filter sets or lasers. Fluorescence is detected upon hybridization.

Example 14

Flow Cytometry

Flow cytometry is used to evaluate CD3 receptors on Jurkat cells with a compound of formula V labeled with Goat Anti-Mouse (GAM) secondary antibody. Jurkat cells are centrifuged for five minutes at 4000 rpm, washed with 1×3 ml dPBS, and resuspended in 5 ml dPBS. Cell concentration is adjusted to $28 \times 10^6$ cells/ml. Cells are incubated for 45 minutes in mouse anti-CD3 antibody (0.625 μg/ml), centrifuged for five minutes and washed with 2×1 ml PBS. Cells are incubated for 45 min in formula V-goat anti-mouse conjugate diluted in dPBS (2.7 μg/ml). Cells are then centrifuged as previously described, washed 2×1 ml in dPBS, and resuspended in 300 μl dPBS. Data are collected on a Becton Dickinson FACSCalibur® or equivalent flow cytometer. Antigens on individual cells are quantitatively detected with high precision, speed, and accuracy.

Example 15

Reagent Kit for High Content Screening (HCS) and/or High Content Analysis (HCA) Assays Any of the above described compounds are conjugated to antibodies, and are prepared as a kit for HCS and/or HCA for a specific biology. The kit contains instructions for used in a validated protocol.

Example 16

High Content Screening (HCS)

Any of the above described compounds are conjugated to antibodies and used for HCS measurement of p53 induction. A549 cells are seeded at 5,000 cells/well on 96 well microplates one day before treating them with different concentrations of camptothecin. In the presence of the drug, cells are incubated for 18-20 hours at 37° C., 5% $CO_2$ in a humidified incubator. Cells are then fixed with 4% paraformaldehyde, permeabilized with 0.1% Triton X-100, and then labeled with rabbit p53 primary antibody and goat-anti-rabbit-conjugate of one of the above-described compounds. Cell nuclei are labeled with Hoechst 33342. The samples are imaged and quantitatively analyzed on an ArrayScan® HCS Reader (Cellomics, Inc. Pittsburgh Pa.). Fluorescence images show p53 induction in the nucleus with 5 μM camptothecin. Untreated cells do not have any p53 signal. Camptothecin treated cells show bright p53 labeling in the nuclei.

Other variations or embodiments will also be apparent to one of ordinary skill in the art from the above description and examples. Thus, the forgoing embodiments are not to be construed as limiting the scope of the following claims.

What is claimed is:

1. At least one compound of formula I or formula II

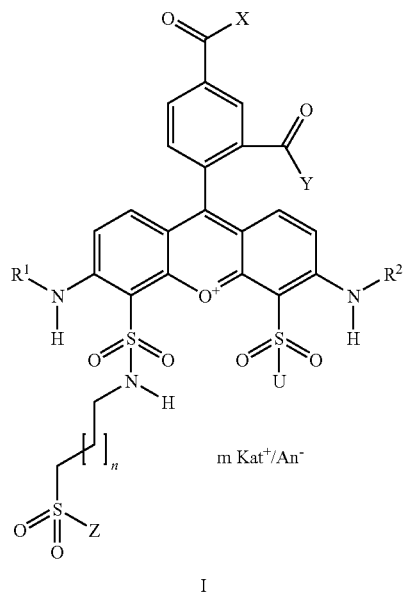

I

-continued

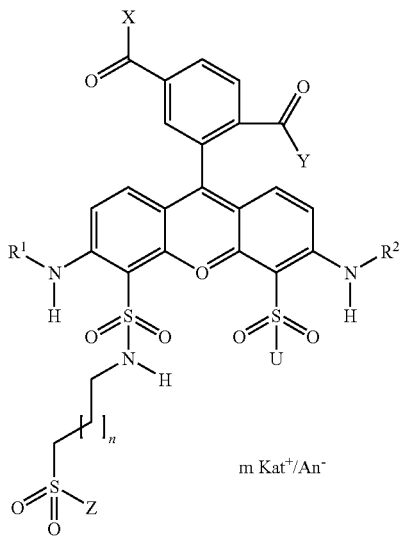

II wherein

R¹ and R² are the same or different and are independently selected from the group consisting of —H, —$C_1$-$C_{18}$-alkyl or -ω-sulfoalkyl;

X and Y are the same or different and are independently selected from the group consisting of —O⁻, —OH, —SH, —NH—NH₂, —F, —Cl, —Br, —I, —O-Su (succinimidyl/sulfosuccinimidyl), —O-STP (4-sulfo-2,3,5,6-tetrafluorophenyl), —O-TFP (2,3,5,6-tetrafluorophenyl), —O-benzotriazole, -benzotriazole, —NR—CO—CH₂—I, —NR₂, —NR-biomolecule, —NR-L-COO⁻, —NR-L-COOH, —NR-L-COO-Su, —NR-L-COO-STP, —NR-L-COO-TFP, —NR-L-CONR₂, —NR-L-CO-biomolecule, —NR-L-CO—NH—NH₂, —NR-L-OH, —NR-L-O-phosphoramidite, —NR-L-CHO, —NR-L-maleimid, or —NR-L-NH—CO—CH₂—I; where R is equal to R¹ and R² and L is selected from the group consisting of a divalent linear (—(CH₂)$_o$—, o=1 to 15), crossed, or cyclic alkane group that can be substituted by at least one atom selected from the group consisting of oxygen, substituted nitrogen, and/or sulfur, and the biomolecule is a protein, antibody, nucleotide, oligonucleotide, biotin, or hapten;

Z is —O⁻ or OH;

U is —O⁻, —OH or NH-L-SO₂Z;

Kat is Li, Na, K, ammonium (mono-, di- or trialkyl) or another cation;

An is F, Cl, Br, I, BF₄, ClO₄, CH₃CO₂, CF₃CO₂ or another anion;

m is an integer from 1-6 necessary to compensate the negative or positive charge from the dye moiety in formula I or formula II; and n is an integer from 0-12.

2. A compound selected from at least one of formula III, formula IV, formula V, formula VI, formula VII, formula VIII, formula IX, formula X, formula XI, formula XII, formula XIII, formula XIV, formula XV, or formula XVI

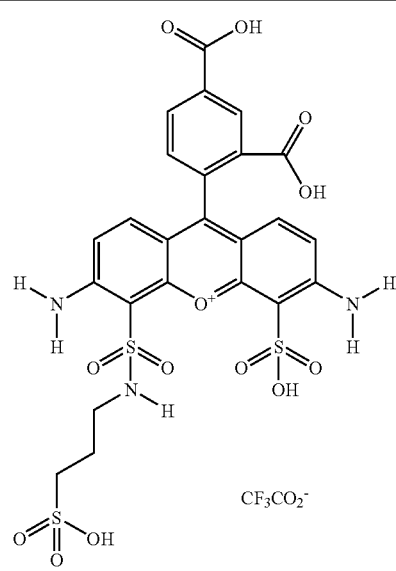

III (V03-04093)

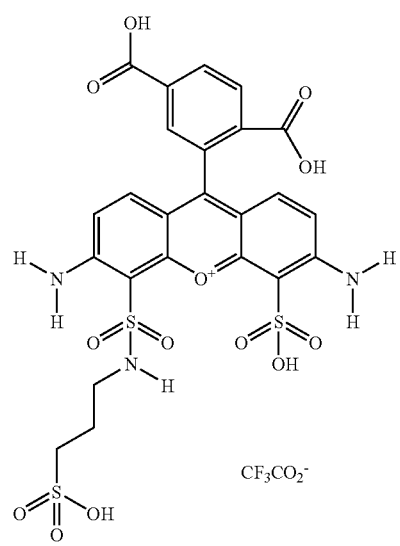

IV

-continued
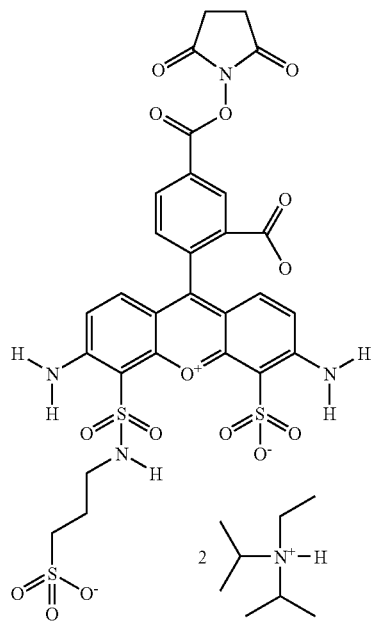
V (V03-04115)
-continued
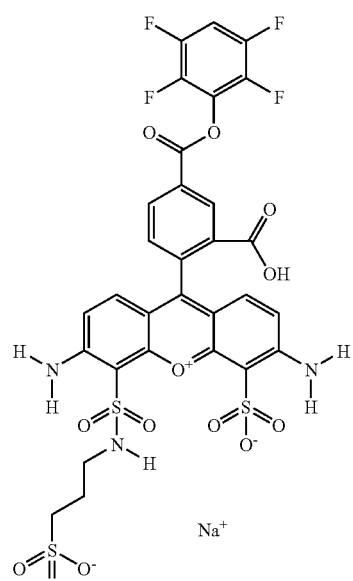
VII (V03-04153)
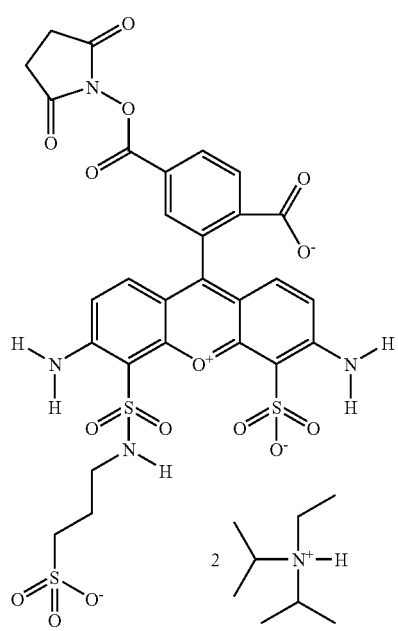
VI
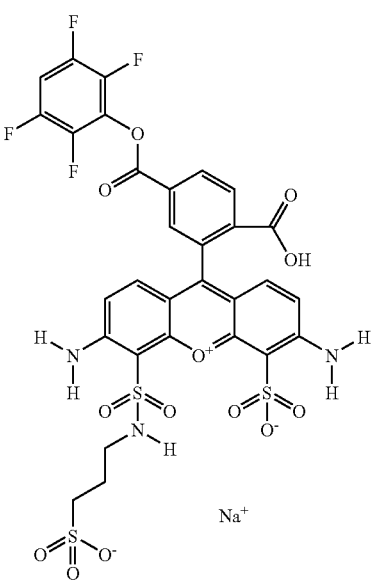
VIII -continued
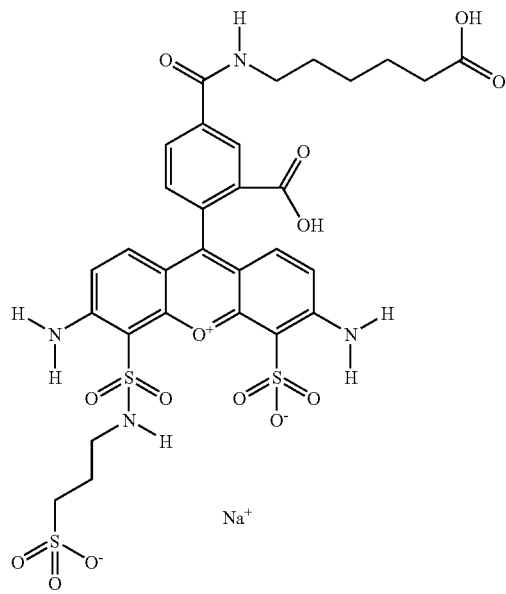
IX (V02-06158)
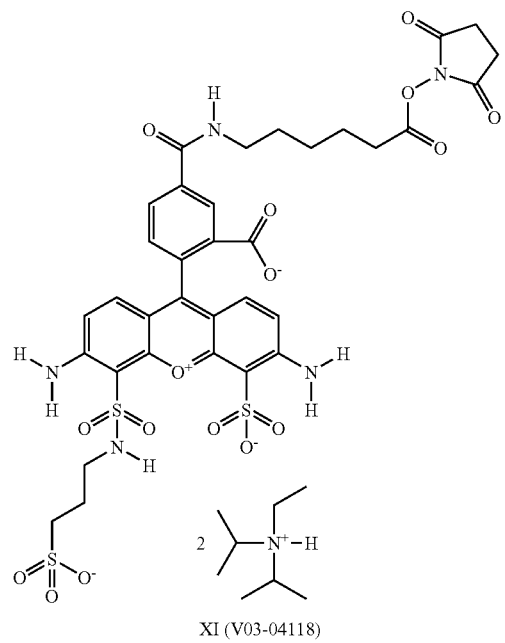
XI (V03-04118)
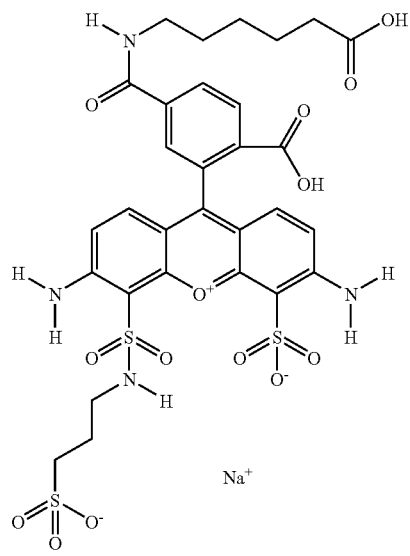
X
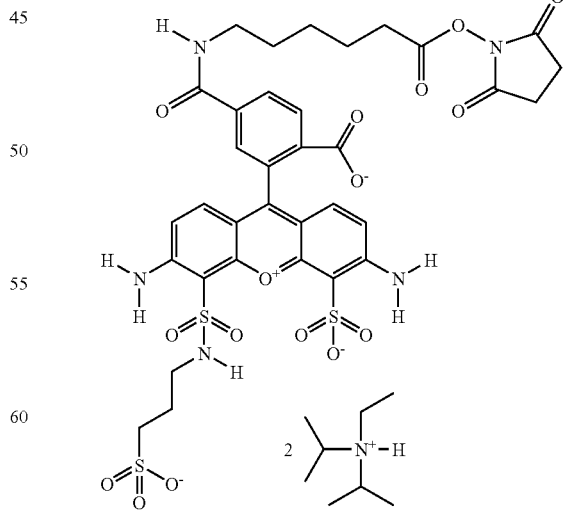
XII -continued
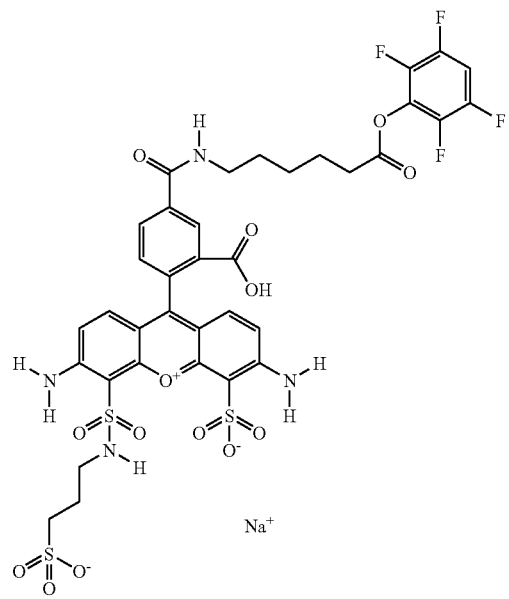
XIII (V03-04120)
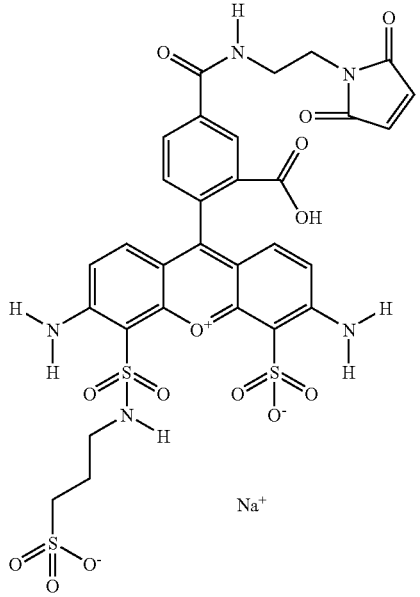
XV (V03-04133)
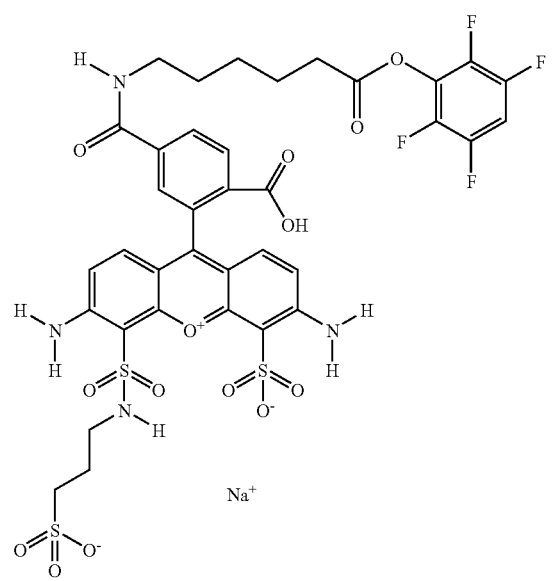
XIV
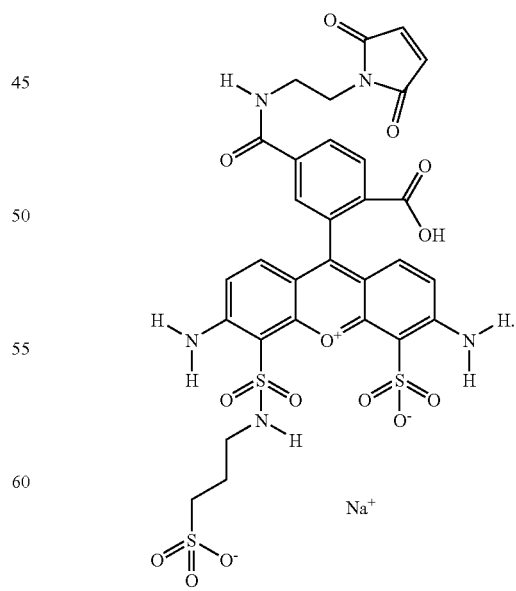
XVI 3. A biocompatible dye composition comprising at least one excipient and a compound selected from at least one of formula I or formula II

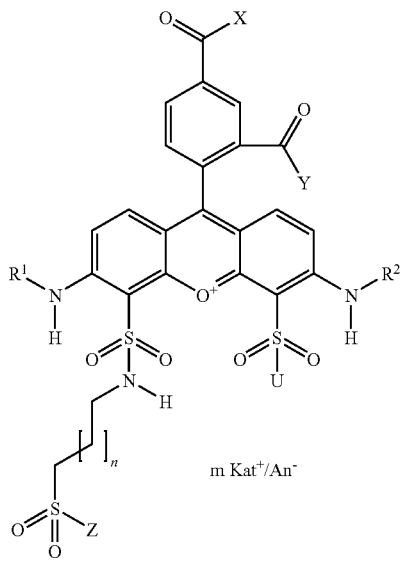

I

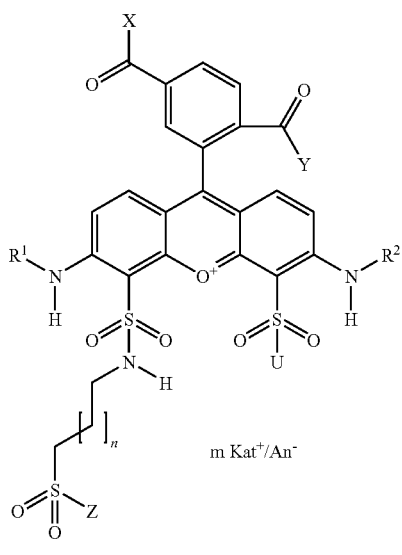

II resulting in a biocompatible dye composition, wherein $R^1$ and $R^2$ are the same or different and are independently selected from the group consisting of —H, —$C_1$-$C_{18}$-alkyl or -ω-sulfoalkyl;

X and Y are the same or different and are independently selected from the group consisting of —O⁻, —OH, —SH, —NH—$NH_2$, —F, —Cl, —Br, —I, —O-Su (succinimidyl/sulfosuccinimidyl), —O-STP (4-sulfo-2,3,5,6-tetrafluorophenyl), —O-TFP (2,3,5,6-tetrafluorophenyl), —O-benzotriazole, -benzotriazole, —NR—CO—$CH_2$—I, —$NR_2$, —NR-biomolecule, —NR-L-COO⁻, —NR-L-COOH, —NR-L-COO-Su, —NR-L-COO-STP, —NR-L-COO-TFP, —NR-L-$CONR_2$, —NR-L-CO-biomolecule, —NR-L-CO—NH—$NH_2$, —NR-L-OH, —NR-L-O-phosphoramidite, —NR-L-CHO, —NR-L-maleimid, or —NR-L-NH—CO—$CH_2$—I; where R is equal to $R^1$ and $R^2$ and L is selected from the group consisting of a divalent linear (—$(CH_2)_o$—, o=1 to 15), crossed, or cyclic alkane group that can be substituted by at least one atom selected from the group consisting of oxygen, substituted nitrogen, and/or sulfur, and the biomolecule is a protein, antibody, nucleotide, oligonucleotide, biotin, or hapten;

Z is —O⁻ or OH;

U is —O⁻, —OH or NH-L-$SO_2$Z;

Kat is Li, Na, K, ammonium (mono-, di- or trialkyl) or another cation;

An is F, Cl, Br, I, $BF_4$, $ClO_4$, $CH_3CO_2$, $CF_3CO_2$ or another anion;

m is an integer from 1-6 necessary to compensate the negative or positive charge from the dye moiety in formula I or formula II; and n is an integer from 0-12.

4. A biocompatible dye composition comprising at least one excipient and a compound selected from the group consisting of formula III, formula IV, formula V, formula VI, formula VII, formula VIII, formula IX, formula X, formula XI, formula XII, formula XIII, formula XIV, formula XV, formula XVI, and combinations thereof, resulting in a biocompatible dye composition, wherein

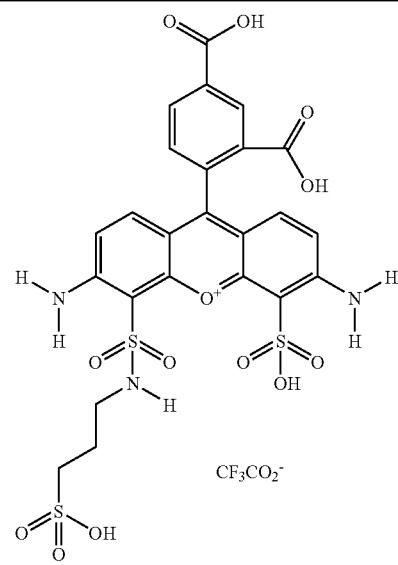

III (V03-04093)

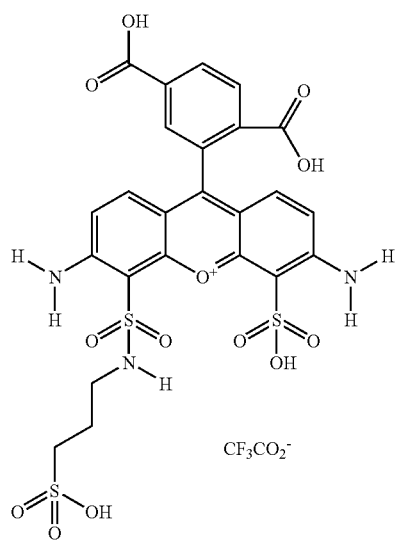
IV
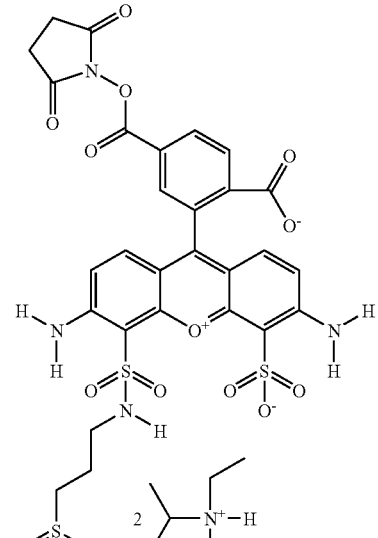
VI
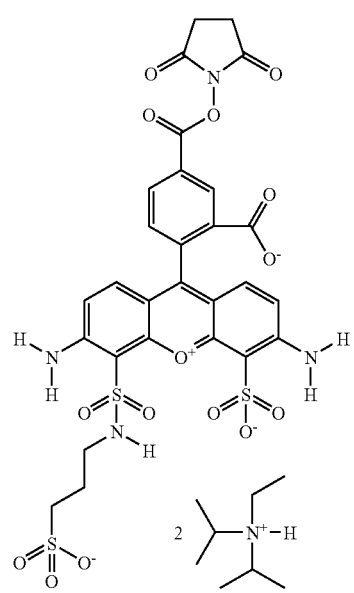
V (V03-04115)
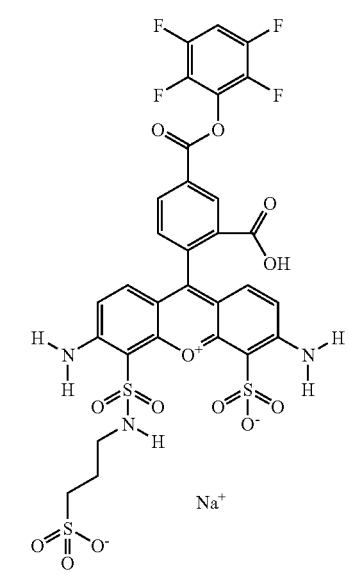
VII (V03-04153)

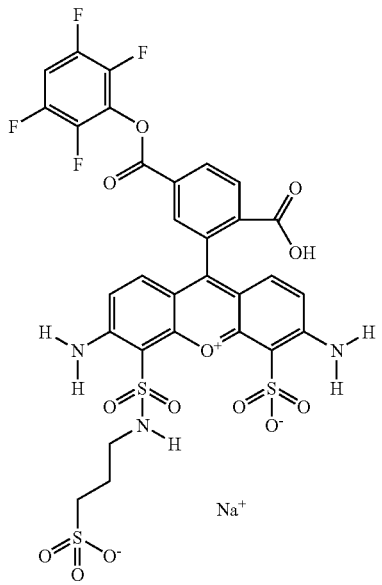
VIII
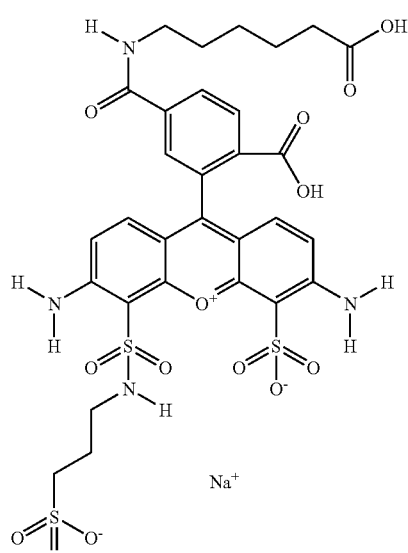
X
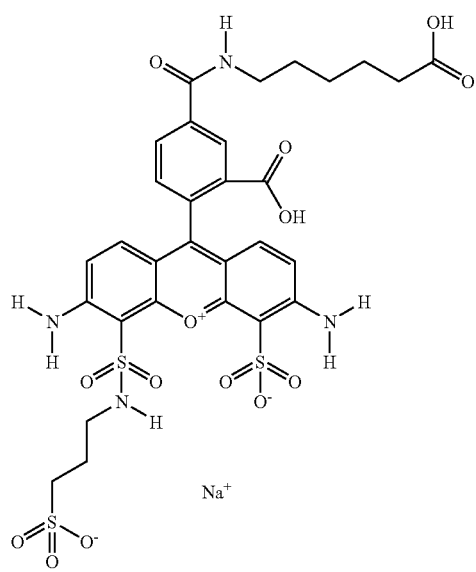
IX (V02-06158)
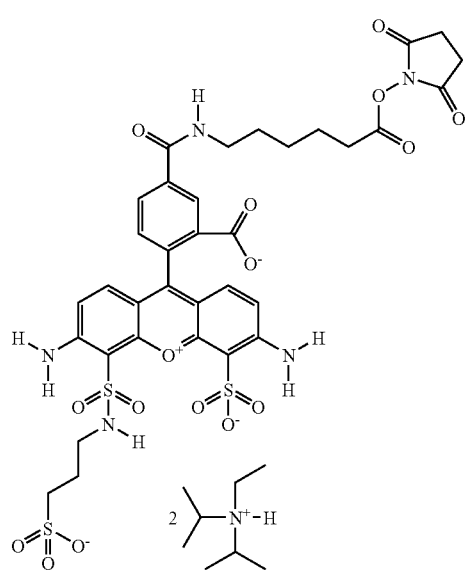
XI (V03-04118)

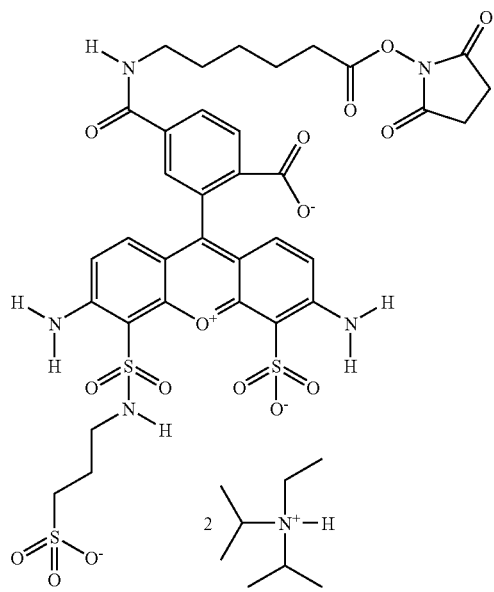
XII
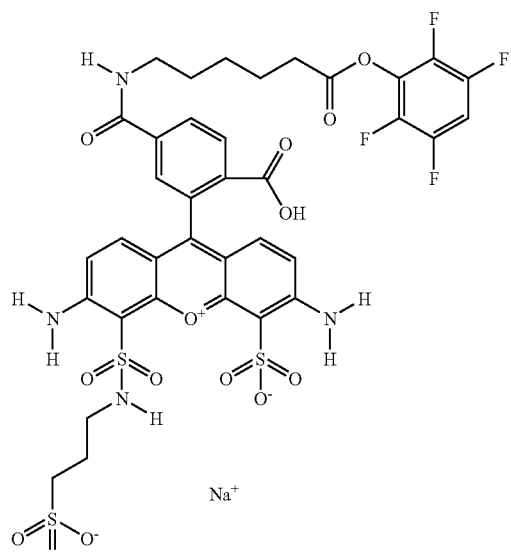
XIV
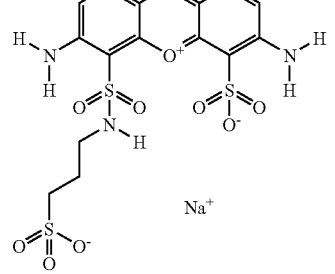
XIII (V03-04120)
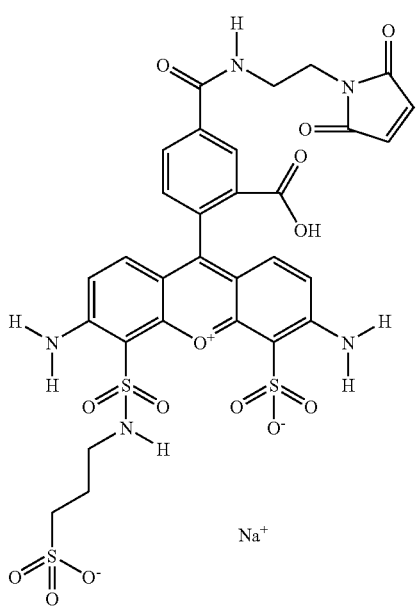
XV (V03-04133)

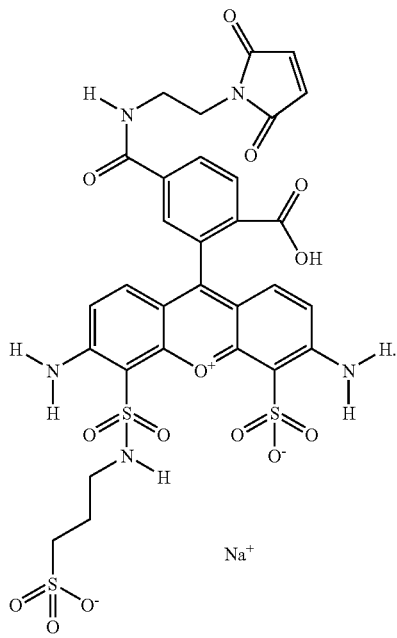

XVI

5. A method of labelling at least one biomolecule, the method comprising providing a composition comprising at least one excipient and a compound of at least one of formula I or formula II

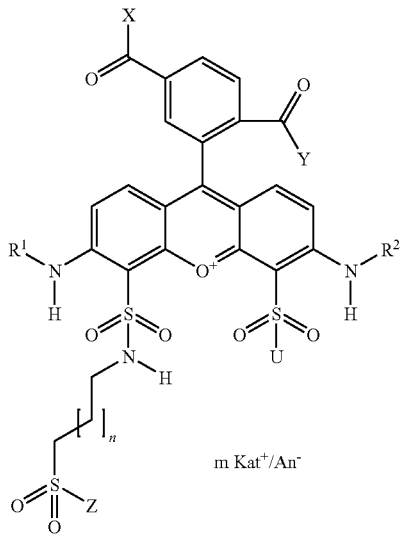

I

II in an effective concentration to a biomolecule under conditions sufficient for conjugating the compound to the biomolecule, and detecting the biomolecule-bound conjugate, wherein $R^1$ and $R^2$ are the same or different and are independently selected from the group consisting of —H, —$C_1$-$C_{18}$-alkyl or -ω-sulfoalkyl;

X and Y are the same or different and are independently selected from the group consisting of —O⁻, —OH, —SH, —NH—$NH_2$, —F, —Cl, —Br, —I, —O-Su (succinimidyl/sulfosuccinimidyl), —O-STP (4-sulfo-2,3,5,6-tetrafluorophenyl), —O-TFP (2,3,5,6-tetrafluorophenyl), —O-benzotriazole, -benzotriazole, —NR—CO—$CH_2$—I, —$NR_2$, —NR-biomolecule, —NR-L-COO⁻, —NR-L-COOH, —NR-L-COO-Su, —NR-L-COO-STP, —NR-L-COO-TFP, —NR-L-$CONR_2$, —NR-L-CO-biomolecule, —NR-L-CO—NH—$NH_2$, —NR-L-OH, —NR-L-O-phosphoramidite, —NR-L-CHO, —NR-L-maleimid, or —NR-L-NH—CO—$CH_2$—I; where R is equal to $R^1$ and $R^2$ and L is selected from the group consisting of a divalent linear (—$(CH_2)_o$—, o=1 to 15), crossed, or cyclic alkane group that can be substituted by at least one atom selected from the group consisting of oxygen, substituted nitrogen, and/or sulfur, and the biomolecule is a protein, antibody, nucleotide, oligonucleotide, biotin, or hapten;

Z is —O⁻ or OH;

U is —O⁻, —OH or NH-L-$SO_2$Z;

Kat is Li, Na, K, ammonium (mono-, di- or trialkyl) or another cation;

An is F, Cl, Br, I, $BF_4$, $ClO_4$, $CH_3CO_2$, $CF_3CO_2$ or another anion;

m is an integer from 1-6 necessary to compensate the negative or positive charge from the dye moiety in formula I or formula II; and n is an integer from 0-12.

6. A method of labelling at least one biomolecule, the method comprising providing a composition comprising at least one excipient and a compound of at least one of formula III, formula IV, formula V, formula VI, formula VII, formula VIII, formula IX, formula X, formula XI, formula XII, formula XIII, formula XIV, formula XV, formula XVI, and combinations thereof, in an effective concentration to a biomolecule under conditions sufficient for conjugating the compound to the biomolecule, and detecting the biomolecule-bound conjugate, wherein

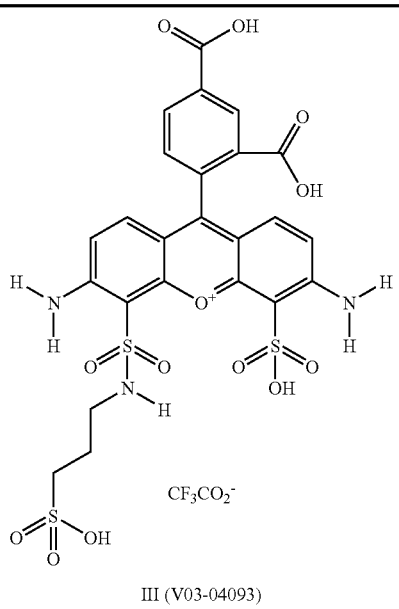

III (V03-04093)

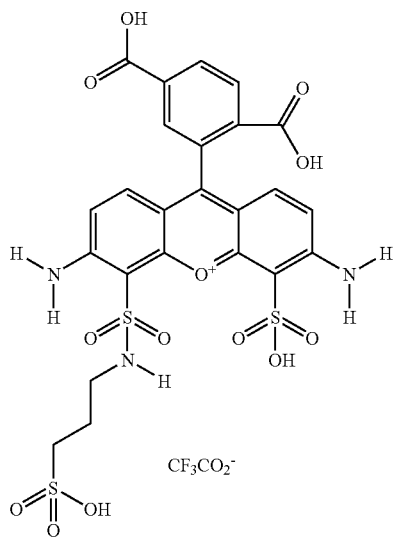

IV

-continued

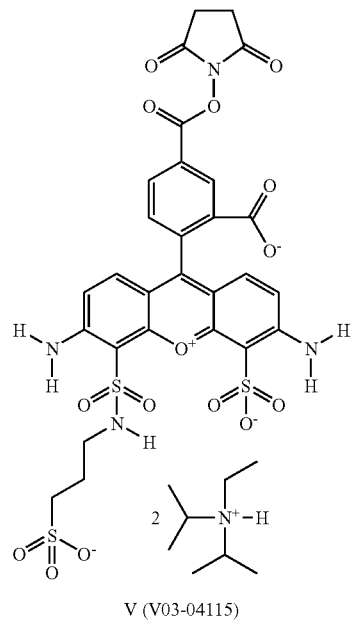

V (V03-04115)

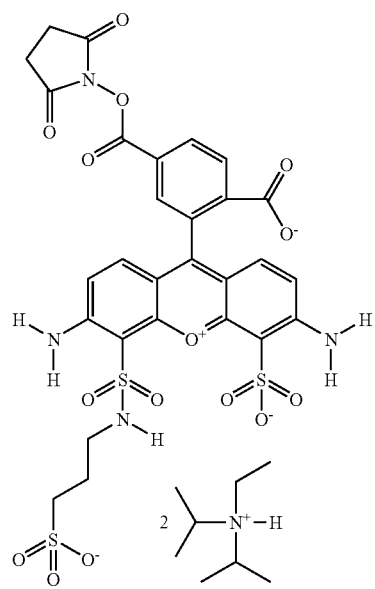

VI

-continued
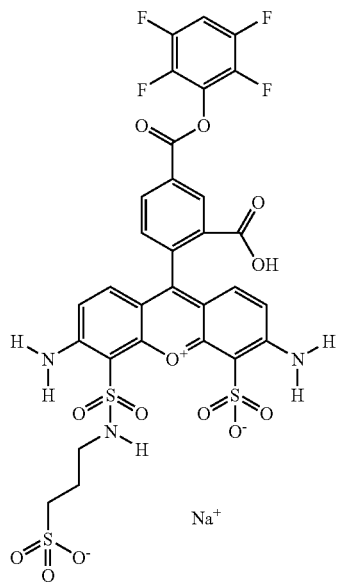
VII (V03-04153)
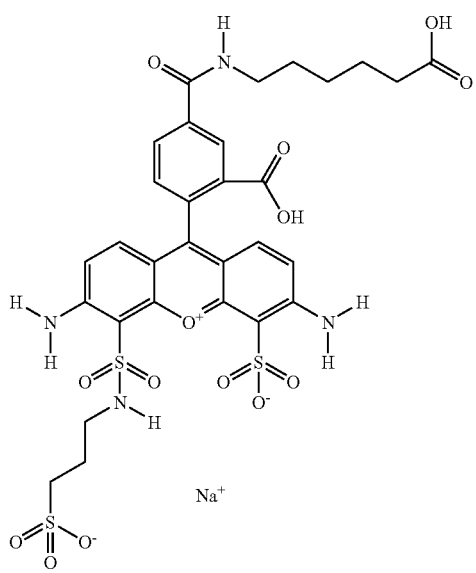
IX (V02-06158)
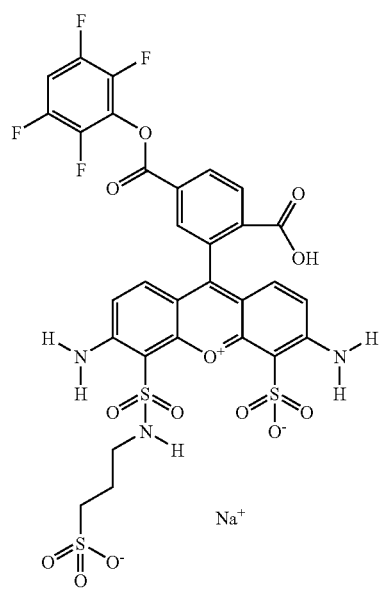
VIII
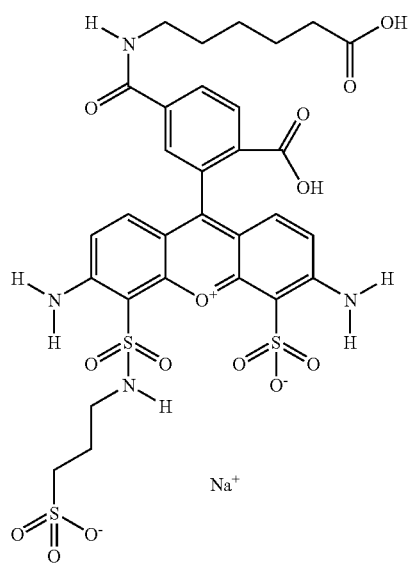
X -continued
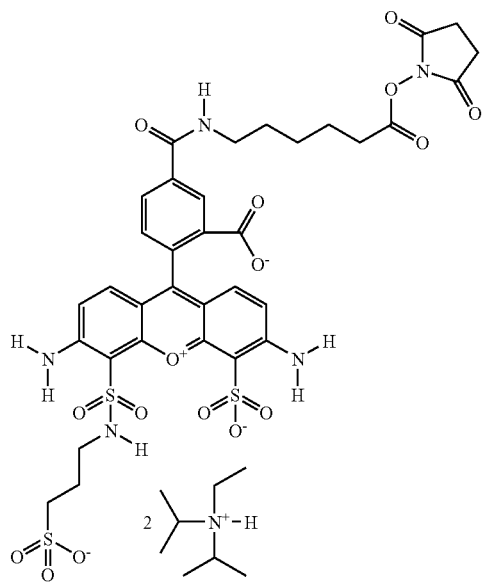
XI (V03-04118)
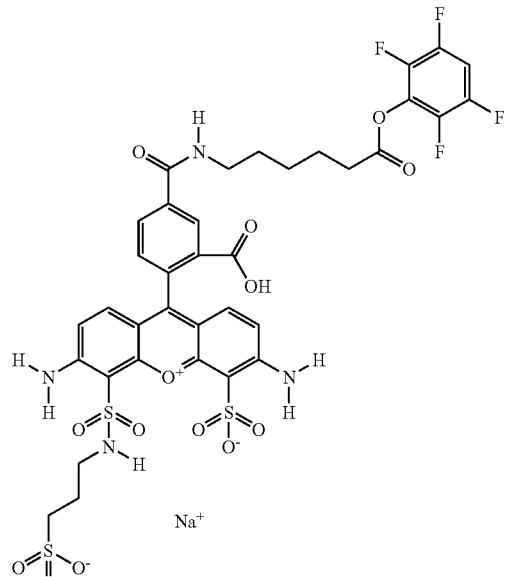
XIII (V03-04120)
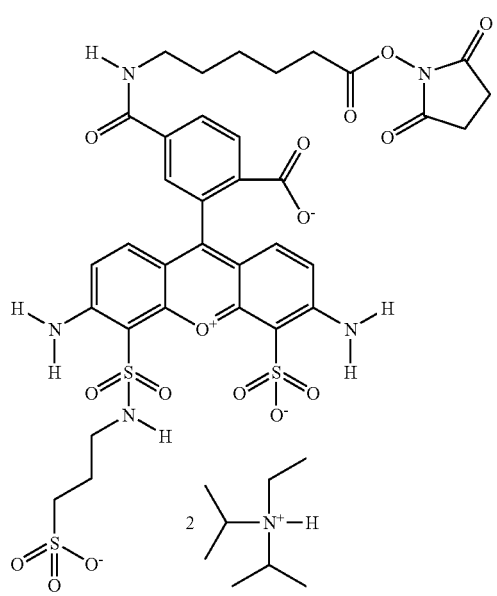
XII
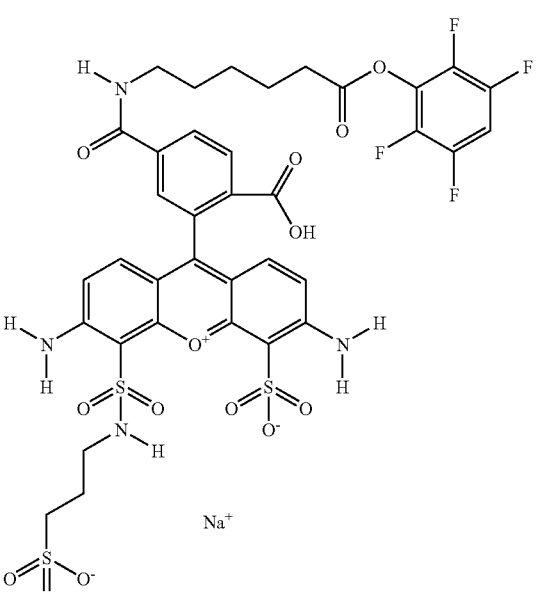
XIV -continued

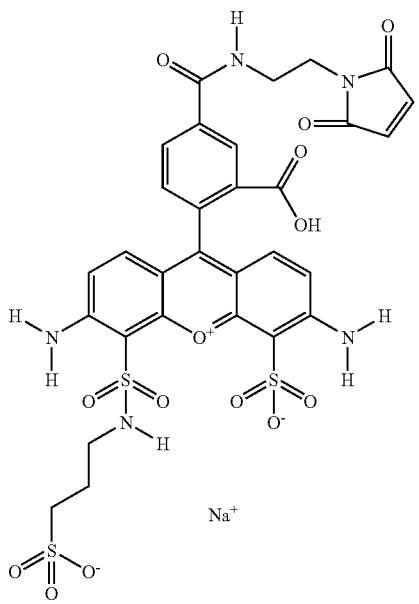

XV (V03-04133)

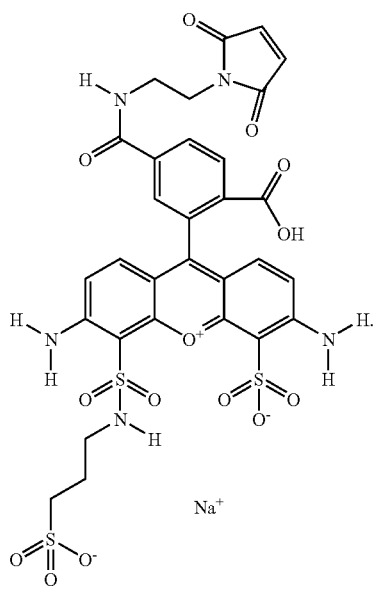

XVI

7. The method of either claim 5 or claim 6 used in at least one of a protein assay, immunofluorescence assay, singleplex application, or multiplex application.

8. The method of either claim 5 or claim 6 used in a multiplex application in combination with other fluorescent dyes or conjugates.

9. The method of either claim 5 or claim 6 wherein the compound is rendered reactive prior to conjugation.

10. The method of either claim 5 or claim 6 wherein the compound further comprises L-Rt where L is a linker group covalently attached to the compound and Rt is a reactive group that is capable of covalently linking to the biomolecule.

11. The method of either claim 5 or claim 6 wherein the biomolecule is selected from at least one of a protein, antibody, nucleotide, oligonucleotide, biotin, or hapten.

12. The compound of formula V (V03-04115)

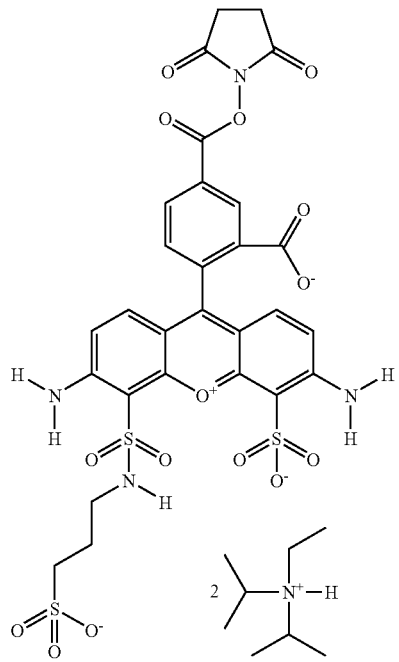

in a composition capable of use as a fluorescent dye in a biological assay.

13. The compound of claim 12 detected as a biomolecule conjugate.

14. The compound of claim 12 in a kit with instructions for use in a protein assay.

* * * * *